(12) United States Patent \
Miller

(10) Patent No.: US 11,717,642 B2 \
(45) Date of Patent: Aug. 8, 2023

(54) CATHETER INCLUDING ONE OR MORE SENSORS

(71) Applicant: Covidien LP, Mansfield, MA (US)

(72) Inventor: David J. Miller, Boulder, CO (US)

(73) Assignee: Covidien LP, Mansfield, MA (US)

( * ) Notice: Subject to any disclaimer, the term of this patent is extended or adjusted under 35 U.S.C. 154(b) by 310 days.

(21) Appl. No.: 16/858,287

(22) Filed: Apr. 24, 2020

(65) Prior Publication Data

US 2021/0330935 A1 Oct. 28, 2021

(51) Int. Cl.
*A61M 25/00* (2006.01)
*A61M 25/01* (2006.01)

(52) U.S. Cl.
CPC ........ *A61M 25/0017* (2013.01); *A61M 25/01* (2013.01); *A61M 2025/0166* (2013.01);
(Continued)

(58) Field of Classification Search
CPC .............. A61M 25/0017; A61M 25/01; A61M 2025/0166; A61M 2205/3331; A61M 2205/3368; A61M 2205/3379; A61M 2210/1085; A61M 2210/1089; A61M 2202/0496; A61M 2230/50; A61M 25/10; A61M 25/04; A61M 1/75; A61M 1/76; A61M 1/77; A61M 1/774; A61M 39/105; A61M 2205/3334; A61M 2205/3344; A61M 1/74; A61M 2205/3306; A61M 2205/7545; A61M 1/743; A61M 1/84; A61B 5/01; A61B 5/14507; A61B 5/20; A61B 5/208; A61B 5/6852; A61B 5/6853; A61B 5/1459; A61B 5/1473; A61B 5/207;

(Continued)

(56) References Cited

U.S. PATENT DOCUMENTS 4,448,207 A 5/1984 Parrish \
5,389,217 A 2/1995 Singer \
(Continued)

FOREIGN PATENT DOCUMENTS

WO 2004/100788 A1 11/2004 \
WO WO-2004100788 A1 * 11/2004 ......... A61B 5/14507 \
(Continued)

OTHER PUBLICATIONS

International Search Report and Written Opinion of International Application No. PCT/US2021/028676, dated Jul. 23, 2021, 15 pp.
(Continued)

*Primary Examiner* — Kai H Weng \
*Assistant Examiner* — Brandon W. Levy \
(74) *Attorney, Agent, or Firm* — Shumaker & Sieffert, P.A.

(57) ABSTRACT

In one example, a system includes an elongated body defining a lumen where the elongated body includes a proximal portion and a distal portion. An anchoring member may be positioned on the proximal portion of the elongated body. The system further includes a sensor located on the elongated body where the sensor may be configured to sense at least one flow parameter of a fluid within the lumen. In some examples, the system includes processing circuitry configured to determine at least one of a density parameter or a temperature parameter of the fluid in the lumen based on the sensed at least one flow parameter of the fluid.

20 Claims, 13 Drawing Sheets

(52) U.S. Cl.
CPC .............. *A61M 2205/3331* (2013.01); *A61M 2205/3368* (2013.01); *A61M 2205/3379* (2013.01); *A61M 2210/1085* (2013.01); *A61M 2210/1089* (2013.01)

(58) Field of Classification Search
CPC ... A61B 5/0031; A61B 5/0215; A61B 5/0261; A61B 2562/0271; A61B 5/027; A61B 10/007; A61B 2018/00791; A61B 17/22; A61B 17/00; A61B 17/32037; A61B 17/3498; A61B 90/06; A61B 2017/00022; A61B 2017/00561; A61B 2090/064; A61B 2217/005; A61B 2017/22079; A61B 2018/00744; G01N 33/493
See application file for complete search history.

(56) References Cited

U.S. PATENT DOCUMENTS

| | | | |
|---|---|---|---|
| 5,463,906 | A | 11/1995 | Spani et al. |
| 5,916,153 | A | 6/1999 | Rhea, Jr. et al. |
| 6,053,873 | A | 4/2000 | Govari et al. |
| 6,406,452 | B1 | 6/2002 | Westerbeck |
| 8,715,254 | B2 | 5/2014 | Nishtala |
| 8,827,924 | B2 | 9/2014 | Paz et al. |
| 9,655,555 | B2 | 5/2017 | Burnett et al. |
| 9,662,058 | B2 | 5/2017 | Burnett et al. |
| 9,857,210 | B2 | 1/2018 | Mantinband et al. |
| 10,307,564 | B2 | 6/2019 | Erbey, II et al. |
| 10,433,790 | B2 | 10/2019 | Ofek et al. |
| 10,506,965 | B2 | 12/2019 | Cooper et al. |
| 10,524,694 | B2 | 1/2020 | Hunter |
| 10,542,923 | B2 | 1/2020 | Chang et al. |
| 2004/0215067 | A1 | 10/2004 | Stiger et al. |
| 2006/0100743 | A1 | 5/2006 | Townsend et al. |
| 2009/0043184 | A1 | 2/2009 | Fjield et al. |
| 2009/0105799 | A1 | 4/2009 | Hekmat et al. |
| 2009/0143673 | A1 | 6/2009 | Drost et al. |
| 2009/0285761 | A1 | 11/2009 | Wang et al. |
| 2010/0116048 | A1 | 5/2010 | Fulkerson et al. |
| 2010/0204765 | A1 | 8/2010 | Hall et al. |
| 2011/0046514 | A1 | 2/2011 | Greenwald et al. |
| 2011/0208013 | A1 | 8/2011 | Phan et al. |
| 2013/0030262 | A1* | 1/2013 | Burnett .............. A61B 5/14539 600/484 |
| 2013/0041234 | A1 | 2/2013 | Grinstein et al. |
| 2013/0237901 | A1 | 9/2013 | Woo |
| 2015/0093307 | A1 | 4/2015 | Gaines et al. |
| 2015/0105659 | A1* | 4/2015 | Salahieh ................ A61M 5/007 604/21 |
| 2015/0366462 | A1 | 12/2015 | Ramos et al. |
| 2016/0183819 | A1 | 6/2016 | Burnett et al. |
| 2016/0258798 | A1 | 9/2016 | Muhammad et al. |
| 2016/0310711 | A1 | 10/2016 | Luxon et al. |
| 2017/0035342 | A1 | 2/2017 | Elia et al. |
| 2017/0079571 | A1 | 3/2017 | Washington |
| 2017/0113000 | A1 | 4/2017 | Tobescu et al. |
| 2017/0348512 | A1 | 12/2017 | Orr et al. |
| 2017/0367636 | A1 | 12/2017 | Mantinband et al. |
| 2018/0110455 | A1 | 4/2018 | Chang et al. |
| 2018/0188097 | A1 | 7/2018 | Levine |
| 2019/0069831 | A1 | 3/2019 | Kuck et al. |
| 2019/0076674 | A1 | 3/2019 | Ergun et al. |
| 2019/0150801 | A1 | 5/2019 | Suehara et al. |
| 2019/0316948 | A1 | 10/2019 | Karol et al. |
| 2019/0343445 | A1 | 11/2019 | Burnett et al. |
| 2019/0358387 | A1 | 11/2019 | Elbadry et al. |
| 2020/0022636 | A1 | 1/2020 | Suehara et al. |
| 2020/0022638 | A1 | 1/2020 | Suehara et al. |
| 2020/0085378 | A1 | 3/2020 | Burnett et al. |
| 2021/0330230 | A1 | 10/2021 | Miller |
| 2021/0330231 | A1 | 10/2021 | Miller |
| 2021/0330934 | A1 | 10/2021 | Miller |
| 2022/0015676 | A1 | 1/2022 | Miller |

FOREIGN PATENT DOCUMENTS

| | | | |
|---|---|---|---|
| WO | 2012/176194 A1 | | 12/2012 |
| WO | 2014/043650 A2 | | 3/2014 |
| WO | WO-2018208734 A1 | * | 11/2018 |
| WO | 2019/140224 A2 | | 7/2019 |
| WO | 2020/033752 A1 | | 2/2020 |

OTHER PUBLICATIONS

"Flow measurement", Wikipedia, the Free Encyclopedia, last edited on Jan. 2, 2020, accessed on Jul. 28, 2020, 17 pp.
U.S. Appl. No. 16/858,321, filed Apr. 24, 2020, by Miller.
Office Action from U.S. Appl. No. 16/858,209 dated Jan. 4, 2023, 22 pp.
Office Action from U.S. Appl. No. 16/858,252 dated Jan. 5, 2023, 16 pp.
International Preliminary Report on Patentability from International Application No. PCT/US2021/028676 dated Nov. 3, 2022, 9 pp.
Office Action from U.S. Appl. No. 16/858,233 dated Aug. 31, 2022, 44 pp.
Office Action from U.S. Appl. No. 16/858,321 dated Oct. 14, 2022, 11 pp.
Final Office Action from U.S. Appl. No. 16/858,252 dated May 22, 2023, 17 pp.
Response to Office Action dated Jan. 4, 2023 from U.S. Appl. No. 16/858,209, filed Apr. 3, 2023, 11 pp.
Response to Office Action dated Jan. 5, 2023 from U.S. Appl. No. 16/858,252, filed Apr. 3, 2023, 11 pp.

* cited by examiner

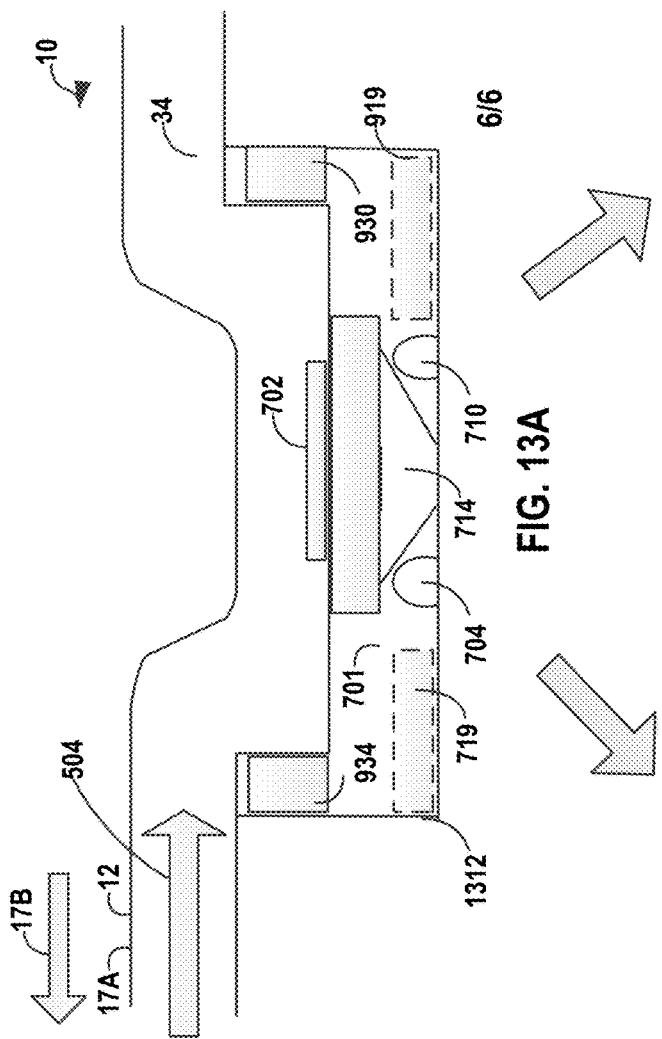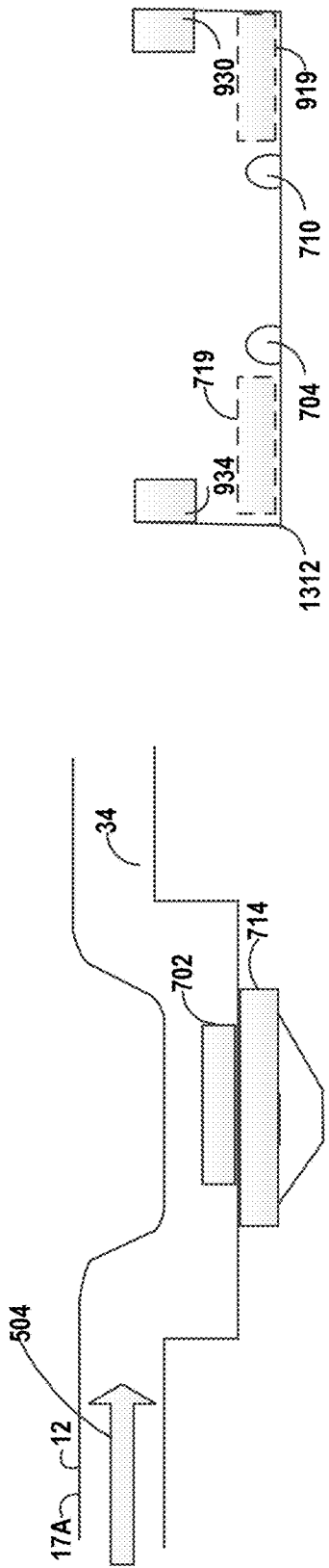
FIG. 13A
FIG. 13B

CATHETER INCLUDING ONE OR MORE SENSORS

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter used for longer time periods than a non-Foley catheter. Some Foley catheters are constructed of silicon rubber and include an anchoring member, which may be an inflatable balloon inflated in a patient's bladder to serve as an anchor, so a proximal end of the catheter does not slip out of the patient's bladder.

SUMMARY

The disclosure describes catheters (e.g., a Foley catheter) and techniques for making and using such catheters. The catheters may include one or more sensor configured to sense one more parameters of fluid within a lumen of the catheter.

In one example, the disclosure relates to a device comprising an elongated body defining a lumen where the elongated body comprises a proximal portion and a distal portion. An anchoring member may be positioned on the proximal portion of the elongated body. A first temperature sensor may be configured to sense a first temperature of a fluid at a first location in the lumen. A second temperature sensor may be configured to sense a second temperature of the fluid at a second location in the lumen where the first location is proximal to the second location. A heating member located proximal to the second temperature sensor where the heating member is configured to heat the fluid within the lumen.

In another example, the disclosure relates to a method comprising heating, with a heating member a fluid within a lumen defined by an elongated body comprising a proximal portion and a distal portion. A first temperature sensor may sense a first temperature of a fluid at a first location in the lumen. A second temperature sensor may sense a second temperature of the fluid at a second location in the lumen where the first location is proximal to the second location.

In another example, the disclosure relates to a device comprising an elongated body defining a lumen where the elongated body comprises a proximal portion and a distal portion. An anchoring member may be positioned on the proximal portion of the elongated body. A first temperature sensor may be configured to sense a first temperature of a fluid at a first location in the lumen. A second temperature sensor may be configured to sense a second temperature of the fluid at a second location in the lumen, the first location being proximal to the second location. A heating member may be located proximal to the second temperature sensor where the heating member may be configured to heat the fluid within the lumen. Processing circuitry may be configured to determine a flow of the fluid within the lumen based on a difference between the first temperature and the second temperature. An oxygen sensor may be configured to sense oxygen concentration in the fluid within the lumen where the oxygen sensor is configured to be calibrated based on at least one of the first sensed temperature or the second sensed temperature.

In one example, the disclosure relates to a medical device system comprising an elongated body defining a lumen where the elongated body comprising a proximal portion and a distal portion. A sensor coupled to the elongated body where the sensor comprises a first ultrasonic sensor configured to transmit a first ultrasonic signal in a first direction through a fluid flowing distally within the lumen. The sensor comprising a second ultrasonic sensor configured to transmit a second ultrasonic signal in a second direction through the fluid flowing distally within the lumen where the second ultrasonic sensor may be positioned on the elongated body proximal to the first ultrasonic sensor. The first ultrasonic sensor is configured to receive the second ultrasonic signal transmitted through the fluid flowing in the lumen. The second ultrasonic sensor is configured to receive the first ultrasonic sound transmitted through the fluid flowing in the lumen.

In another example, the disclosure relates to a method comprising transmitting, with a first ultrasonic sensor, a first ultrasonic signal in a first direction through a fluid flowing distally within a lumen defined by an elongated body comprising a proximal portion and a distal portion. A second ultrasonic sensor being positioned on the elongated body proximal to the first ultrasonic sensor, transmitting a second ultrasonic signal in a second direction through the fluid flowing distally within the lumen. The first ultrasonic sensor, receiving the second ultrasonic signal transmitted through the fluid flowing in the lumen. The second ultrasonic sensor, receiving the first ultrasonic sound transmitted through the fluid flowing in the lumen.

In another example, the disclosure relates to a medical device system comprising an elongated body defining a lumen where the elongated body comprises a proximal portion and a distal portion. A sensor coupled to the elongated body where the sensor comprises a first ultrasonic sensor configured to transmit a first ultrasonic signal in a first direction through a fluid flowing distally within the lumen. The sensor comprising a second ultrasonic sensor configured to transmit a second ultrasonic signal in a second direction through the fluid flowing distally within the lumen where the second ultrasonic sensor may be positioned on the elongated body proximal to the first ultrasonic sensor. Processing circuitry configured to determine a first transit time of the first ultrasonic signal where the first transit time is a time from transmission from the first ultrasonic sensor to reception by the second ultrasonic sensor. The processing circuitry configured to determine a second transit time of the second ultrasonic signal where the second transit time is a time from transmission from the second ultrasonic sensor to reception by the first ultrasonic sensor. The processing circuitry configured to determine a flow velocity of the fluid through the lumen based on the determined first and second transit times of the first and the second ultrasonic signals. The first ultrasonic sensor is configured to receive the second ultrasonic signal transmitted through the fluid flowing in the lumen. The second ultrasonic sensor is configured to receive the first ultrasonic sound transmitted through the fluid flowing in the lumen.

In one example, the disclosure relates to a system comprising an elongated body defining a lumen where the elongated body comprises a proximal portion and a distal portion. An anchoring member positioned on the proximal portion of the elongated body. The system further comprising a fluorescence material configured to be located within the lumen with a fluid in the lumen. A light source configured to emit light to expose the fluorescence material to the emitted light where the fluorescence material within the fluid is configured to fluoresce when exposed to the light in the lumen. The system further comprising a light detector configured to detect the fluorescence of the fluorescence material. The system configured to detect oxygen in the fluid within the lumen based on the detected fluorescence In another example, the disclosure relates to a method comprising controlling a light source to emit light to expose a fluorescence material to the emitted light where the fluorescence material within a fluid is configured to fluoresce when exposed to the light in the lumen defined by an elongated body comprising a proximal portion and a distal portion. Detecting, with a light detector, the fluorescence of the fluorescence material. Determining, based on the detected fluorescence, oxygen in the fluid within the lumen.

In another example, the disclosure relates to a system comprising an elongated body defining a lumen where the elongated body comprises a proximal portion and a distal portion. The system further comprising an anchoring member positioned on the proximal portion of the elongated body. The system comprising a fluorescence material configured to be located within the lumen with a fluid in the lumen. A light source configured to emit light to expose the fluorescence material to the emitted light where the fluorescence material within the fluid is configured to fluoresce when exposed to the light in the lumen. A light detector configured to detect the fluorescence of the fluorescence material. A sensor body configured to be releasably coupled to the elongated body, the sensor body supporting the light source and the light detector. A lens configured to be placed on the elongated body in between the fluorescence material and light source. A first ultrasonic sensor configured to transmit a first ultrasonic signal in a first direction through a fluid flowing distally within the lumen. A second ultrasonic sensor configured to transmit a second ultrasonic signal in a second direction through the fluid flowing distally within the lumen where the second ultrasonic sensor may be positioned on the elongated body proximal to the first ultrasonic sensor. The system is configured to detect oxygen in the fluid within the lumen based on the detected fluorescence.

In one example, the disclosure relates to a system comprising an elongated body defining a lumen where the elongated body comprising a proximal portion and a distal portion. An anchoring member may be positioned on the proximal portion of the elongated body. The system further comprising a sensor located on the elongated body where the sensor may be configured to sense at least one flow parameter of a fluid within the lumen. Processing circuitry configured to determine at least one of a density parameter or a temperature parameter of the fluid in the lumen based on the sensed at least one flow parameter of the fluid.

In another example, the disclosure relates to a method comprising sensing, with a sensor located on an elongated body defining a lumen where the elongated body comprises a proximal portion and a distal portion, at least one flow parameter of a fluid within the lumen. The method further comprising, determining, with processing circuitry, at least one of a density parameter or a temperature parameter of the fluid in the lumen based on the sensed at least one flow parameter of the fluid.

In another example, the disclosure relates to a system comprising an elongated body defining a lumen where the elongated body comprises a proximal portion and a distal portion. An anchoring member may be positioned on the proximal portion of the elongated body. The system further comprising a sensor located on the elongated body where the sensor may be configured to sense at least one flow parameter of a fluid within the lumen. Processing circuitry may be configured to determine at least one of a density parameter or a temperature parameter of the fluid in the lumen based on the sensed at least one flow parameter of the fluid. The system further comprising a temperature sensor configured to determine a temperature of the fluid within the lumen where the processing circuitry is configured to determine the density parameter of the fluid based on the at least one flow parameter and the determined temperature of the fluid.

In one example, the disclosure relates to a catheter system comprising an elongated body defining a lumen where the elongated body comprises a proximal portion and a distal portion. An anchoring member may be positioned on the proximal portion of the elongated body. The system further comprising at least one sensor configured to be coupled to the elongated body where the at least one sensor may be configured to sense one or more parameters of a fluid within the lumen of the elongate body. Memory configured to be coupled to the elongated body where the memory may be configured to store sensor calibration information. The system configured to calibrate the at least one sensor based on the sensor calibration information stored by the memory.

In another example, the disclosure relates to a method comprising sensing, with at least one sensor configured to be coupled to an elongated body defining a lumen and the elongated body comprising a proximal portion and a distal portion, one or more parameters of a fluid within the lumen of the elongate body. Storing, with a memory configured to be coupled to the elongated body, sensor calibration information. The method further comprising calibrating the at least one sensor based on sensor calibration information stored by the memory.

In another example, the disclosure relates to a catheter system comprising an elongated body defining a lumen where the elongated body comprises a proximal portion and a distal portion. An anchoring member may be positioned on the proximal portion of the elongated body. The system further comprising a flow sensor configured to sense a flow rate of the fluid in the lumen. An oxygen sensor configured to sense the amount of oxygen within the fluid in the lumen. The system further comprising memory configured to be coupled to the elongated body where the memory may be configured to store sensor calibration information. The system is configured to calibrate the flow sensor and/or the oxygen sensor based on the sensor calibration information stored by the memory.

The details of one or more examples are set forth in the accompanying drawings and the description below. Other features, objects, and advantages will be apparent from the description and drawings, and from the claims.

BRIEF DESCRIPTION OF DRAWINGS

FIG. 13A is a diagram illustrating an example combination ultrasonic flow sensor and oxygen sensor for an elongated body according to techniques of this disclosure.

FIG. 13B is a diagram illustrating the example combination ultrasonic flow sensor and oxygen sensor of FIG. 13A separated into a disposable portion and a reusable portion according to techniques of this disclosure.

DETAILED DESCRIPTION

Figure 1:
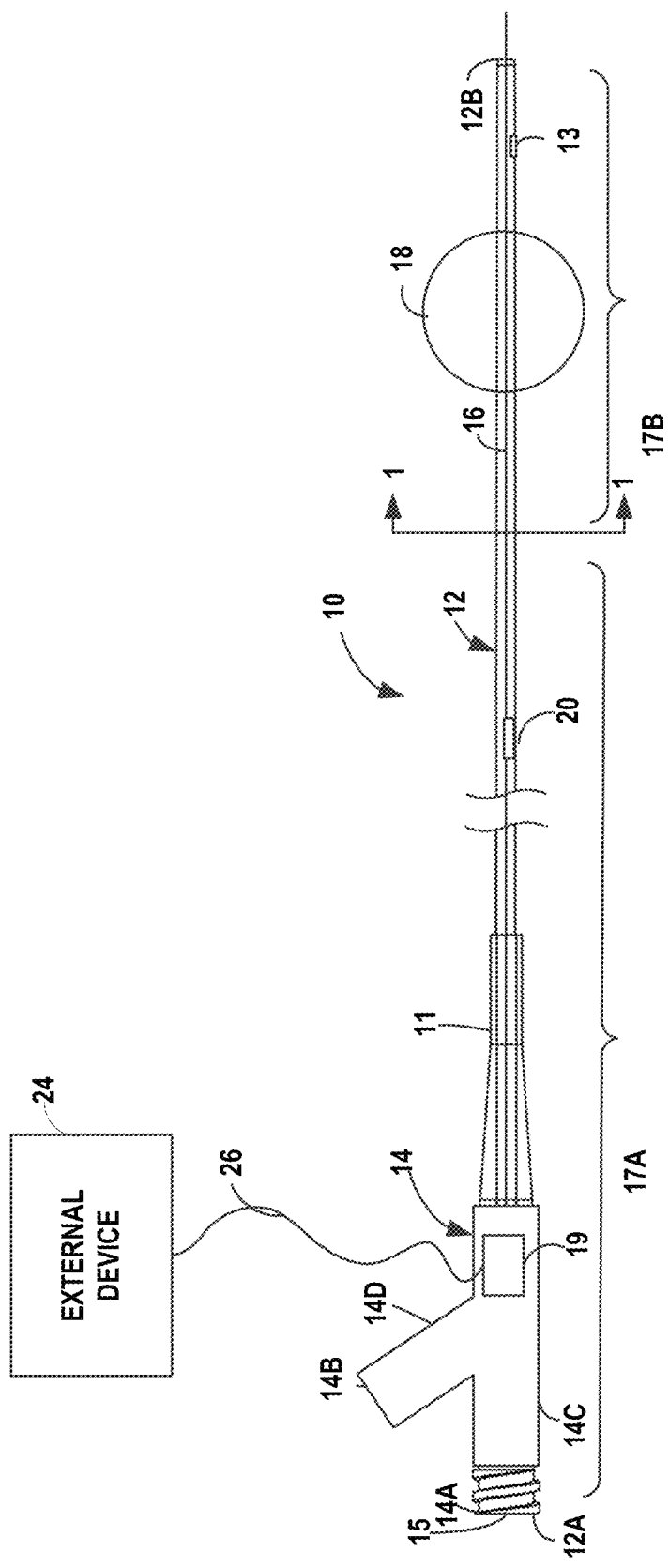
FIG. 1 is a diagram illustrating an example medical device.

In general, the disclosure describes a medical device and systems including a catheter, such as a Foley catheter or other urinary or non-urinary catheter, and methods of making and using the same. As will be described below, examples of the disclosure may include catheters having one or more sensors configured to sense one or more parameters of a fluid such as urine within a lumen of the catheter body (e.g., the drainage lumen). Example sensed parameters may include flow rate of the fluid, temperature of the fluid, density of the fluid, and/or oxygen content of the fluid. In some examples, the sensed parameters may be used to monitor urine output/rate of urine production of a patient and/or the amount of oxygen dissolved in the urine. Such information may be useful in monitoring the renal function of the patient, e.g., while the catheter is inserted within the patient. In some examples, all or a portion of the sensor(s) may be removably coupled to the catheter body, e.g., such that the catheter body may be disposed after use but all or a portion of the sensor may be reused with another catheter body. For ease of description, examples of the disclosure are primarily described with regard to a catheter such as a Foley catheter being employed as a urinary catheter within a patient. For example, in some instances, the present disclosure is directed to a Foley catheter including one or more sensors configured to facilitate detection and/or quantification of one or more physiological parameters of a patient's urine to determine the urine output of the patient's kidneys (e.g., for renal monitoring). However, examples of the present disclosure are not limited to Foley-type catheters or urinary catheters.

Acute kidney injury (AKI) is a complication that occurs commonly after major surgeries such as cardiac surgery and other operations that are long and involve significant blood loss or fluid shifts. The primary cause of surgery-associated AKI may be hypoxia of the kidneys. Renal hypoxia may cause degradation of renal function, which, after one to three days, e.g., may cause a reduced urine output and/or an accumulation of waste products in the bloodstream. This accumulation of fluid and waste products may delay the recovery of the patient leading to more extended and expensive hospital stays and sometimes requiring renal replacement therapy.

One approach to preventing AKI is to monitor the oxygenation status of a patient's kidneys. However, accurate monitoring may be challenging due to the inaccessibility of the kidneys which are deep in the abdominal cavity. Near-Infrared spectroscopy (NIRS) may measure regional oximetry and may have some utility in infants and slender adults but does not have the depth of penetration and specificity required for most adults.

Systemic vital signs like cardiac output, blood pressure, and hematocrit may be useful but may not always be sufficient to properly monitor the kidneys. When the body becomes stressed, such as during cardiac surgery, blood flow may be reduced to vital organs in a reliable sequence based on the criticality of the organs. It has been observed that the skin may be the first to realize reduced blood flow, followed by the intestines and then the kidneys, then the brain and then the heart. The skin and the intestines may withstand short hypoxic episodes and recover normal function, but the kidneys can be damaged with even brief hypoxic episodes.

Examples of the present disclosure may be related to device features to aid in the monitoring of the kidneys. In some examples, the approach is to monitor the amount of oxygen dissolved in the urine coming from the bladder, as such a measurement may accurately reflects the oxygenation of the kidneys. Such a measurement may be made by monitoring of urine output (rate of urine production) and/or the amount of oxygen dissolved in the urine. Examples of the present disclosure utilize a catheter with one or more sensors that facilitate the determination of such parameters and, thus, allow for the monitoring of the oxygenation status of the kidneys.

As noted above, a Foley catheter may be a type of urinary catheter used in the examples of the present disclosure. A Foley catheter may be modified in the manner described herein to facilitate measurements of urine parameters for renal monitoring. In some examples, one or more sensors may be used in conjunction with a Foley Catheter to monitor renal function to prevent acute kidney injury. In some examples, the sensor(s) may provide data indicating detection of and prevention of acute kidney injury.

FIG. 1 is a conceptual side elevation view of an example medical device 10, which includes elongated body 12, hub 14, and anchoring member 18. In some examples, medical device 10 is a catheter, such as a Foley catheter. While a Foley catheter and its intended use is primarily referred to herein to describe medical device 10, in other examples, medical device 10 may be used for other purposes, such as to drain wounds or for intravascular monitoring or medical procedures.

Medical device 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., so proximal end 12B of elongated body 12 is within the patient's urethra and bladder, distal portion 17A may remain outside of the body of the patient.

As shown in FIG. 1, elongated body 12 may be a body extending from distal end 12A to proximal end 12B and that defines one or more inner lumens. In the example shown in FIGS. 1 and 2, elongated body 12 defines lumen 34 and lumen 36 (shown in FIG. 2). In some examples, lumen 34 may be a drainage lumen for draining a fluid from a target site, such as a bladder. In other examples lumen 34 may be used for any other suitable purpose, such as to deliver a substance or another medical device to a target site within a patient. Lumen 34 may extend from fluid opening 13 to fluid opening 14A. Both fluid opening 13 and fluid opening 14A may be fluidically coupled to lumen 34, so a fluid may flow from one of fluid opening 13 or fluid opening 14A to the other of fluid opening 13 or fluid opening 14A through lumen 34. In the example where lumen 34 is a drainage lumen, fluid opening 13 and fluid opening 14A may be drainage openings. In the example shown in FIG. 1, distal end 12A of elongated body 12 is received within hub 14 and is mechanically connected to hub 14 via an adhesive, welding, or another suitable technique or combination of techniques.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal and proximal portions of elongated body 12 may each have any suitable length.

Hub 14 is positioned at a distal end of elongated body 12 and defines an opening through which the one or more inner lumens (e.g., lumen 34 shown in FIG. 2) of elongated body 12 may be accessed and, in some examples, closed. While hub 14 is shown in FIG. 1 as having two arms, 14C and 14D, (e.g., a "Y-hub"), hub 14 may have any suitable number of arms, which may depend on the number of inner lumens defined by elongated body 12. For example, each arm may be fluidically coupled to a respective inner lumen of elongated body 12. In the example of FIG. 1, hub 14 comprises a fluid opening 14A, which is fluidically coupled to lumen 34, and an inflation opening 14B, which is fluidically coupled to an inflation lumen 36 (shown in FIG. 2) of elongated body 12. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A and an opening 14B via which a clinician may access the deployment mechanism.

In examples in which medical device 10 is a Foley catheter, a fluid collection container (e.g., a urine bag) may be attached to fluid opening 14A for collecting urine draining from the patient's bladder. Inflation opening 14B may be operable to connect to an inflation device to inflate anchoring member 18 positioned on proximal portion 17B of medical device 10. Anchoring member 18 may be uninflated or undeployed when not in use. Hub 14 may include connectors, such as connector 15, for connecting to other devices, such as the fluid collection container and the inflation source. In some examples, medical device 10 includes strain relief member 11, which may be a part of hub 14 or may be separate from hub 14.

Proximal portion 17B of medical device 10 comprises anchoring member 18 and fluid opening 13. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 may include an anchor balloon or other expandable structure. When inflated or deployed, anchoring member 18 may function to anchor medical device 10 to the patient, for example, within the patient's bladder. In this manner, the portion of medical device 10 on the proximal side of anchoring member 18 may not slip out of the patient's bladder. Fluid opening 13 may be positioned on the surface of longitudinal axis of medical device 10 between anchoring member 18 and the proximal end 12B (as shown) or may be positioned at the proximal end 12B.

In accordance with examples of the disclosure, medical device 10 may include one or more sensors which may be configured to monitor one or more parameters of a fluid within lumen 34 (FIG. 2) of elongate body 12. For example, in FIG. 1, medical device includes sensor 20. Sensor 20 may be configured to sense one or more of a temperature, flow rate, light, fluorescence, oxygen, sound, flow velocity, density or specific gravity of a fluid in elongate body 12, e.g., of a fluid within lumen 34 of elongate body 12.

In an example of the present disclosure sensor 20 may be configured to sense the flow rate of urine or other fluid within elongate body 12. For example, as described further below, sensor 20 may be a thermal dilution sensor with a first temperature sensor (e.g., thermocouple or thermistor) that may sense a first temperature of a fluid at a first location in lumen 34, and a second temperature sensor that senses a second temperature of the fluid at a second location in lumen 34 that is different that the first location on elongate body 12, e.g., distal to the first location. Sensor 20 may also include a heating member configured to heat the fluid within the catheter body at a location between the first and second temperature sensor or a location proximal to both the first and second temperature sensors. The heating member heats the fluid and the temperature sensors record the temperature difference of the fluid between the first and second locations. Sensor 20 may then determine the flow rate of the fluid within elongate body 12 based on the sensed temperature difference. For example, the lower the difference in temperature of the fluid between the first and second temperature sensor, the greater the flow rate of the fluid within the elongate body. In some examples, sensor 20 may be used to estimate or otherwise determine a value of the flow rate of the fluid based on the described thermal dilution technique and/or may be used to determine relative changes in flow by comparing changes in thermal decay between the two temperature sensors over a period of time.

As will be described below, in some examples, the temperature sensor(s) of sensor 20 used to determine the flow rate of the fluid within elongated body 12 may also be used for sensing one or more other parameters of the fluid within elongate body 12. For example, temperature sensor 20 may be used in the calibration of an oxygen sensor that uses a fluorescence lifetime material. Oxygen may be sensed using a fluorescence lifetime technique. A fluorescence (or luminescence) material may be exposed to a certain wavelength of light. The fluorescence material may glow or fluoresce when exposed to this wavelength of light. In certain materials, the rate at which the intensity of the fluorescence fades may be inversely proportional to the amount of oxygen in the surrounding fluid. The more oxygen present, the faster the fluorescence fades. By measuring the rate of fluorescence decay, the amount of oxygen can be measured.

Fluorescence material may be temperature-dependent and therefore to obtain a more accurate oxygen measurement it may be helpful to know the temperature of the fluid. The temperature sensed from a thermal dilution flow sensor may be used to calibrate a fluorescence lifetime oxygen sensor. If the oxygen sensor is upstream of the thermal dilution flow sensor, the upstream temperature sensor may be used as the reference for the temperature of the fluid. If the oxygen sensor is downstream of the thermal dilution flow sensor, the downstream temperature sensor may be used as the reference for the temperature of the fluid. Similarly, the flow sensor could be an ultrasonic flow sensor. An ultrasonic flow sensor may also determine the temperature of the fluid and this temperature measurement may be the reference for the temperature of the fluid for the oxygen sensor Additionally or alternatively, sensor 20 may be configured to monitor or otherwise determine the flow of a fluid within elongated body 12 using ultrasonic techniques. For example, sensor 20 may be an ultrasonic flow sensor including a first ultrasonic sensor configured to transmit a first ultrasonic signal in a first direction through a fluid flowing distally within lumen 34, and a second ultrasonic sensor configured to transmit a second ultrasonic signal in a second direction through the fluid flowing distally within lumen 34, where the second ultrasonic sensor may be positioned on the elongated body proximal to the first ultrasonic sensor. In such an example, the first ultrasonic sensor of sensor 20 may receive the second ultrasonic signal transmitted through the fluid flowing in lumen 34. The second ultrasonic sensor of sensor 20 may receive the first ultrasonic sound transmitted through the fluid flowing in the lumen. By comparing the transit time with the flow and against the flow directions, sensor 20 may determine an average velocity of the fluid. In some examples, the volumetric flow rate (e.g., measured in ml/min or ml/hour) of the fluid may then be calculated from the flow velocity.

As will be described below, in some examples, when sensor 20 is in the form of an ultrasonic flow sensor, sensor 20 may configured as a reusable sensor that may be used with multiple different catheters. For example, one or more components of sensor 20 may be removably coupled to elongate body 12 so that those components may be removed from elongated body, e.g., when medical device 10 is removed from a patient, and then removably coupled to a similar medical device to function in the same or similar manner as an ultrasonic flow sensor. In this manner, one or more relatively expensive components of sensor 20 may be used with multiple catheters rather than using those components in a single use manner with only one catheter. Ultrasonic sensors may be expensive, and their cost prohibitive to use in a single-use medical device. Further, the ultrasonic flow sensor may also determine the temperature of the fluid and this temperature measurement could be the reference for the temperature of the fluid for the fluorescence lifetime oxygen sensor discussed above.

Additionally, or alternatively, sensor 20 may be configured to sense or otherwise monitor the composition of a fluid (e.g., the amount or concentration of oxygen within the fluid) within elongated body 12 using a fluorescence lifetime technique. For example, sensor 20 may include a fluorescence material that may be located within lumen 34, and a light source configured to emit light to expose the fluorescence material to the emitted light. In such a configuration, the fluorescence material within the fluid may fluoresce when exposed to the light in lumen 34. Sensor 20 may also include a light detector configured to detect the fluorescence of the fluorescence material. Sensor 20 may be configured to detect oxygen in the fluid within lumen 34 based on the detected fluorescence. For example, the fluorescence material may glow or fluoresce when exposed to the light. The fluorescence material may be platinum octaethylporphyrin (PtOEP), phosphors such as palladium (Pd)-porphyrin, PdTPTBP/PtTPTBP (e.g., palladium(ii)/platinum(ii) tetraphenyltetrabenzoporphyrin); Ir(Cs)$_2$acac (e.g., iridium(iii) bis-(benzothiazol-2-yl)-7-(diethylamino)-coumarin-(acetylacetonate)); and/or Ru-dpp (e.g., ruthenium(ii) tris-4,7-diphenyl-1,10-phenanthroline). In some materials, the rate at which the fluoresce fades is inversely proportional to the amount of oxygen it is exposed to. In such materials, the more oxygen present, the faster the fluorescence fades. By measuring the rate of fluorescence decay, sensor 20 may accurately measure the amount of oxygen in the fluid flowing within lumen 34, e.g., on a periodic or substantially continuous basis over a period of time.

In another example of the present disclosure, sensor 20 may be configured to sense at least one flow parameter of a fluid within lumen 34 of elongated body 12 to allow for medical device 10 or other device to determine (e.g., via processing circuitry) at least one of a density parameter or a temperature parameter of the fluid in lumen 34 based on the sensed flow parameter of the fluid. For example, sensor 20 may be a flow sensor where the flow is calculated by measuring the difference in the transit time of sound traveling against the fluid flow and the transit time of sound traveling with the fluid flow. The difference in the transit times in conjunction with dimensions of lumen 34 and the constitution of the fluid may be used to calculate the volumetric flow rate of the fluid. In addition, the average transit time of the upstream and downstream sound can be used to calculate characteristics of the fluid; such as temperature and density. By measuring the average transit time in a known geometry (e.g., lumen 34), changes in density and temperature can be calculated. For example, the temperature may be measured by a different means (e.g., a thermal dilution flow sensor) and this temperature may be used to calculate the density of the fluid. In another example, the density of the urine may be measured using the average transit time when flow is high and the fluid is assumed to be at body temperature (e.g., 98.6° F.). In another example, body temperature may be measured using a sensor at proximal end 12B, from other body temperature measuring devices, or assumed to be normal. The density of fluids, usually represented as the specific gravity, may be an important and common measurement (e.g. urinalysis). For example, the specific gravity of urine can be used to understand a patients' hydration status and the filtration capabilities of patient. The ability to measure urine density continuously and quickly can aid in understanding of the state of patient.

In another example of the present disclosure, sensor 20 may sense one or more parameters of a fluid within lumen 34. Sensor 20 may require calibration information to be accurate. Flow sensors and oxygen sensors may require sensor-specific calibration information to produce an accurate measurement and compensate for variability in sensor 20. Sensor 20 have memory on sensor 20 that stores sensor calibration information that is used by external device 24 to more accurately read sensor data being sent from sensor 20. Additionally, or alternatively, memory 19 may store sensor calibration information to calibrate sensor 20 based on the sensor calibration information stored by memory 19.

Many sensors require calibration information to be accurate. Sensors may provide increasingly accurate measurements with sensor-specific calibration information to compensate for variability in the sensors. For example, a thermal dilution flow sensor may require information that correlates actual flow to measured temperature difference. Variability in the temperature differences may occur due to small differences in the heater member, the thermistors/thermocouples, the lumen dimensions, or the position of the heater elements or thermistors/thermocouples.

Similarly, the fluorescence lifetime oxygen sensor may have calibration parameters related to the fluorescing material used, as well as the specifics of the light source and light detector. Through including the sensor calibration in the sensor or memory 19 accuracy of the measurement may increase. Further, the ability to change components in a sensor or offer different ranges of sensors in the future without changing the monitoring software may provide flexibility.

In some examples, sensor 20 may be representative of a single sensor or multiple sensors. Where sensor 20 may be multiple sensors, the multiple sensors may be located on the elongated body at the same location or at different locations despite being shown at a single location in FIG. 1. Sensor 20 may communicate sensor data to external device 24 via an electrical, optical, wireless or other connection. In some examples, sensor 20 may communicate sensor data to external device 24 through a connection(s) within elongated body 12 of medical device 10 from proximal portion 17B to distal portion 17A via embedded wire(s) or optical cable(s). In other examples, sensor 20 may communicate sensor data to external device 24 via a wireless communication technique.

Sensor 20 may be positioned on distal portion 17A of elongated body 12 of medical device 10 including portions of elongated body 12 positioned distal to distal end 12A connected to a fluid collection container (e.g., a urine bag) or the like. Sensor 20 may be an oxygen sensor utilizing a florescence lifetime technique.

In some examples, sensor 20 is mechanically connected to elongated body 12 or another part of medical device 10 using any suitable technique, such as, but not limited to, an adhesive, welding, by being embedded in elongated body 12, via a crimping band or another suitable attachment mechanism or combination of attachment mechanisms. Sensor 20 may be removably coupled to elongated body 12. That is, sensor 20 may be coupled to elongated body 12 and used for a procedure and then sensor 20 may be removed, coupled to another elongated body and used again. In some examples, elongated body 12 includes a structure distal to a distal end of medical device 10, such as tubing extending between hub 14 and a fluid collection container, which sensor 20 may be coupled to.

In some examples, sensor 20 may be disposable and/or reusable. In some examples, sensor 20 may be disposed of, such as placed into medical waste, when elongated body 12 is through being used for a medical procedure. In some examples, all or a portion of sensor 20 may be reusable and detachable from elongated body 12 so sensor 20, or a portion thereof, may be used again on another elongated body for the same, similar or different procedure. For purposes of the disclosure disposable may be defined as an article intended to be used once, or until no longer useful, and then thrown away. Reusable may be defined as an item which can be used again or more than once. A reusable sensor may be configured such that sensor may be coupled to elongate body 12 so that it functions as described in the examples of the disclosure, subsequently removed from elongate body 12 and then coupled to another elongate body in a manner that allows the sensor to again function as described herein on the another elongated body.

Sensor 20 may be configured to communicate sensor data to an external device 24. External device 24 may be a computing device, such as a workstation, a desktop computer, a laptop computer, a smart phone, a tablet, a server or any other type of computing device configured to receive, process and/or display sensor data. Sensor 20 may communicate sensor data to the external device via a connection 26. Connection 26 may be an electrical, optical, wireless or other connection.

Memory 19 may be located on elongated body 12 or hub 14. In some examples, all or a portion of memory 19 may be removable from elongated body 12 and may be located on or adjacent with sensor 20. Data sensed by sensor 20 may be stored on memory 19, e.g., for later retrieval by external device 24 and/or for processing of the sensor data from sensor 20. While memory 19 is shown as being separate from sensor 20, in some examples, sensor 20 may additionally or alternatively include another memory for storing date from sensor 20.

In some examples, memory 19 may include all or a portion of calibration data for sensor 20. Processing circuitry may store sensor data within memory 19 and communicate this data with external device 24. In some examples, medical device 10 may have processing circuitry on elongated body 12 or hub 14 that may control all or some operations of sensor 20. In some examples, the processing circuitry of external device 24 may control all or some operations of sensor 20. In some examples, the processing circuitry of external device 24 and processing circuitry of medical device 10 may control all or some of operations of sensor 20 together. Memory 19 may also store calibration information for sensor 20. This calibration information may assist in providing calibration information to sensor 20 and thus improve the collecting of more accurate information from sensor 20. Memory 19 may also receive information from external device 24, which memory 19 may retain onboard after disconnection from external device 24. Further, memory 19 may then share this information with another external device in the event external device 24 breaks down or in the more likely event the patient to whom medical device 10 is inserted into may be moved from surgery to an intensive care. In intensive care, memory 19 may now communicate with another external device and share information collected from surgery.

Memory 19 may store program instructions, such as software or algorithms, which may include one or more program modules, which are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Elongated body 12 may be structurally configured to be relatively flexible, pushable, and relatively kink- and buckle-resistant, so it may resist buckling when a pushing force is applied to a relatively distal portion of medical device 10 to advance elongated body 12 proximally through the urethra and into the bladder. Kinking and/or buckling of elongated body 12 may hinder a clinician's efforts to push the elongated body proximally. Any suitable material may be used for elongated body 12, such as a suitable biocompatible polymer or other biocompatible material.

Figure 2:
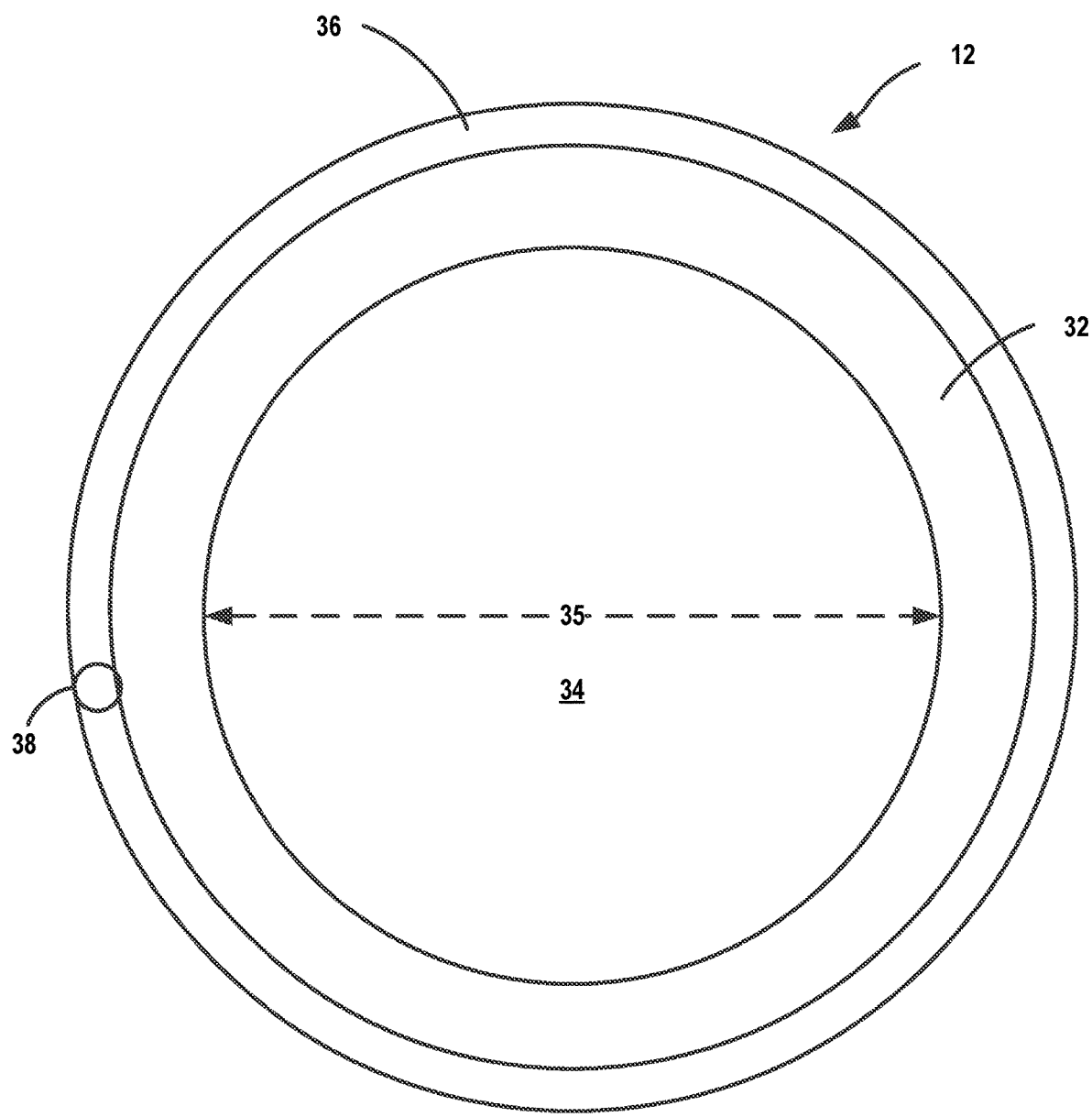
FIG. 2 is a diagram illustrating example a cross-section of the medical device of FIG. 1, the cross-section being take along lines 2-2 of FIG. 1.

FIG. 2 is a diagram illustrating an example cross-section of medical device 10, where the cross-section is taken along line 1-1 in FIG. 1 in a direction orthogonal to central longitudinal axis 16. FIG. 2 depicts a cross section of elongated body 12, which defines lumen 34 and lumen 36. In some examples, lumen 34 may be referred to as a drainage lumen, such as in examples in which medical device 10 is a Foley catheter configured to drain urine from a bladder of a patient, and lumen 36 may be referred to as an inflation lumen in examples in which lumen 36 is configured to deliver an inflation fluid to anchoring member 18. Elongated body 12 may enclose connection 38.

Lumen 34 may serve as a passage for urine entering medical device 10 through fluid opening 13 to fluid opening 14A. In the example shown in FIG. 2, lumen wall 32 is relatively non-permeable to substances of interest, such as oxygen and/or carbon dioxide, and positioned between lumen 36 and lumen 34. In some examples, lumen wall 32 extends along an entire length of lumen 34, while in other examples, lumen wall 32 only extends along only a part of a length of lumen 34, for example, from a portion of lumen 34 intended to be in a patient's bladder during use, which may help maintain a desired level of flexibility of elongated body 12. In addition, as shown in FIG. 2, in some examples, lumen wall 32 extends around an entire outer perimeter of lumen 34 (e.g., an outer circumference in examples in which the inner perimeter is circular in cross-section).

Inflation lumen 36 may serve as a passage for a fluid, such as sterile water or saline, or a gas, such as air, from inflation opening 14B to anchoring mechanism 18. For example, an inflation device (not shown) may pump fluid or gas into inflation lumen 36 through inflation opening 14B into anchoring member 18 so anchoring member 18 is inflated to a size suitable to anchor medical device 10 to the patient's bladder. While inflation lumen 36 is shown as circular in cross section, it may be of any shape. In some examples, there may be a plurality of inflation lumens. For example, a plurality of inflation lumens may substantially surround lumen 34. In some examples, anchoring member 18 may be an expandable structure not an inflatable balloon. In such examples, inflation lumen 36 may be replaced by a deployment mechanism which may permit a clinician to expand the expandable structure. For example, inflation lumen may be replaced by a mechanical device pushed and pulled separately from the medical device 10 by a clinician to expand or retract the expandable structure.

Connection 38 may serve to connect sensor 20 positioned at distal portion 17A to connection 26 and/or memory 19. Connection 38 may be an electrical, optical or other connection. In some examples, connection 38 may comprise a plurality of connections. For example, connection 38 may include one of more wired or optical connections to a temperature sensor and one or more connections to a pressure sensor. In some examples, connection 38 may include one or more power connections to power sensor 20 and one or more communications connections to receive sensor data from sensor 20 and to receive calibration information from memory 19.

In examples of the disclosure, lumen 34 may have a small diameter 35 to increase the transit time of the fluid within lumen 34. In some Foley Catheters, the drainage lumen cross-sectional area may be maximized to maximize the flow rate. Adult Foley Catheters may be, e.g., 12, 14, or 16 French (e.g., with a drainage lumen diameter of about 1.3 mm to about 2.6 mm). For a given flow rate, as the cross-sectional area increases the transit time of fluid through lumen 34 decreases. Drainage lumen 34 may have a relatively small cross-sectional area, e.g., to decrease the flow rate and increase fluid transit time. Through increasing the transit time, physical characteristics of the fluid (e.g., oxygen, temperature, etc.) are preserved which increases the accuracy and utility of measurements. In some examples, diameter 35 may be about 0.75 mm to about 1.25 mm. A small inner diameter 35 of lumen 34 with an increased wall diameter (e.g., thicker walls 32) may contribute to the preservation of sensor measurements by also decreasing the gas permeability of elongated body 12. Further, the diameter of lumen 34 may be continuous over the length of elongate body 12 or it may vary. In some examples, the lumen diameter is tailored based on the location of sensor 20, e.g., to increase the accuracy of the measurement by modifying or otherwise controlling the transit time of the fluid relative to the location at which sensor 20 is sensing the fluid. For example, lumen 34 may decrease in diameter relative to the location of sensor 20 so that the transit time of the fluid decreases in the area that sensor 20 is sensing the fluid. This may be useful with a thermal dilution flow sensor such as that described herein where a decrease in diameter 35 may increase the effect of heating a flowing fluid and better detect the temperature difference. In some examples, a narrow lumen may expand the diameter at a sensor location on the elongated body of the catheter. This expansion of the diameter may increase sensor sensitivity and accuracy by increasing the time the fluid spends at the sensor location.

Figure 3:
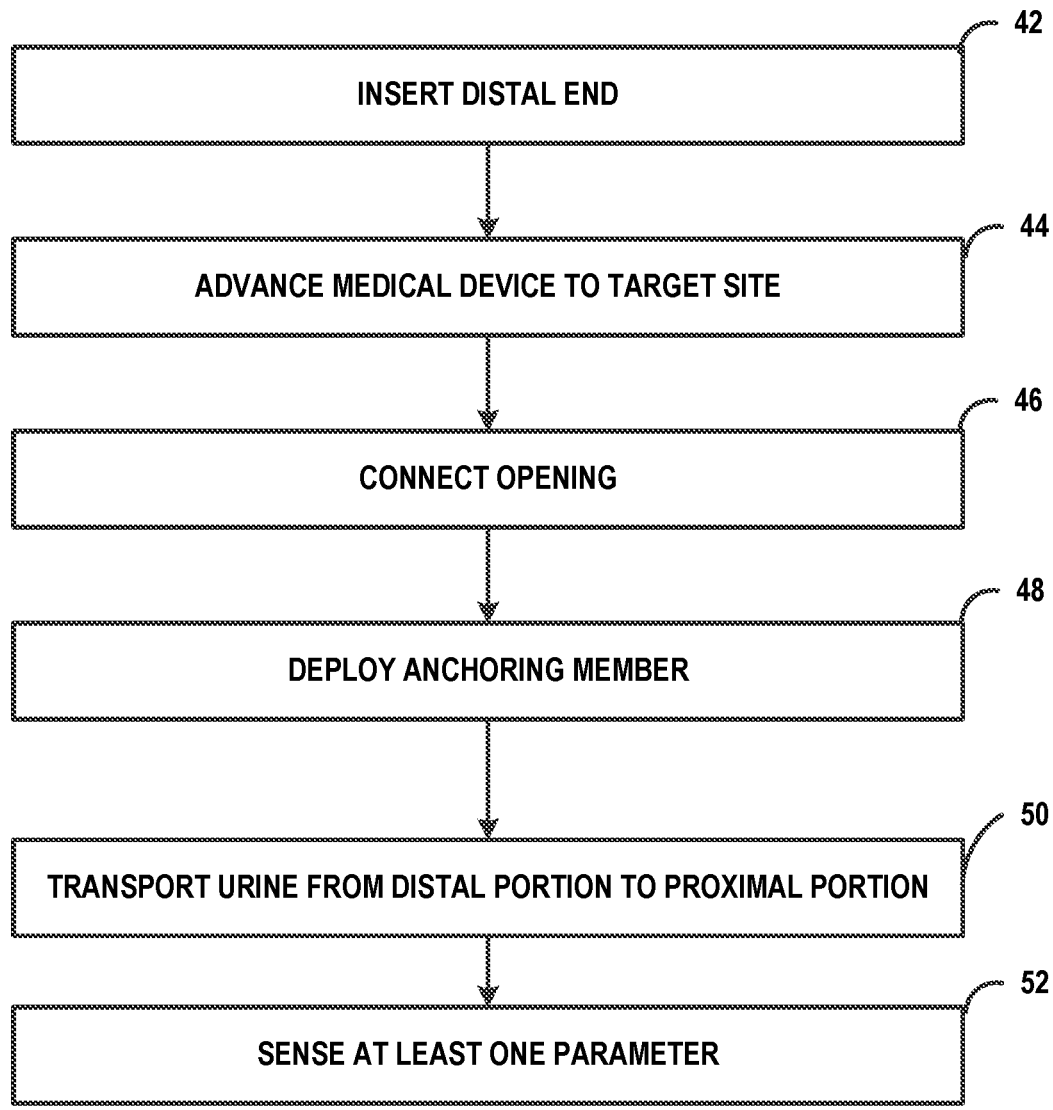
FIG. 3 is a flowchart illustrating an example method of operating a medical device according to the techniques of this disclosure.

FIG. 3 is a flowchart illustrating an example operation of medical device 10. A clinician may insert proximal end 12B of medical device 10 into a patient's urethra (42). The clinician may advance medical device 10 through the patient to a target site (44), e.g., until uninflated or undeployed anchoring member 18 is within the patient's bladder (44). The clinician may connect inflation opening 14B to an inflation device and may connect fluid opening 14A to a fluid collection container and/or to external sensors (46). The clinician may then deploy anchoring member 18 to help secure medical device 10 relative to the target site (48). For example, the clinician may inflate anchoring member 18, for example, using an inflation device and inflation fluid, such as sterile water, saline, or a gas. In examples in which anchoring member 18 is an expandable structure, the clinician may deploy anchoring member 18 by pushing a structure radially outwards or pulling back on a structure to cause the expandable structure to expand radially outwards.

Lumen 34 may transport urine from the proximal portion 17B of medical device 10 to the distal portion 17A of medical device 10 (50). Sensor 20 may sense at least one parameter, such as temperature and/or oxygen, from urine being transported through lumen 34 (52). For example, sensor 20 may sense a parameter such as urine flow (e.g., fluid velocity or volume), and/or amount of dissolved oxygen in the urine. In some examples, sensor 20 may sense at least one parameter between medical device 10 and a fluid collection container, e.g., at the distal end of elongate body 12.

While the example of FIG. 3, sets forth a number of steps, these steps may be performed in a different order or concurrently. For example, the clinician may connect the inflation opening 14B to an inflation device and/or may connect fluid opening 14A to a fluid collection container and/or to sensor 20 prior to inserting the proximal end 12B of medical device 10 into the patient's urethra and lumen 34 may transport urine concurrently with sensor 20 sensing any parameters.

Figure 4:
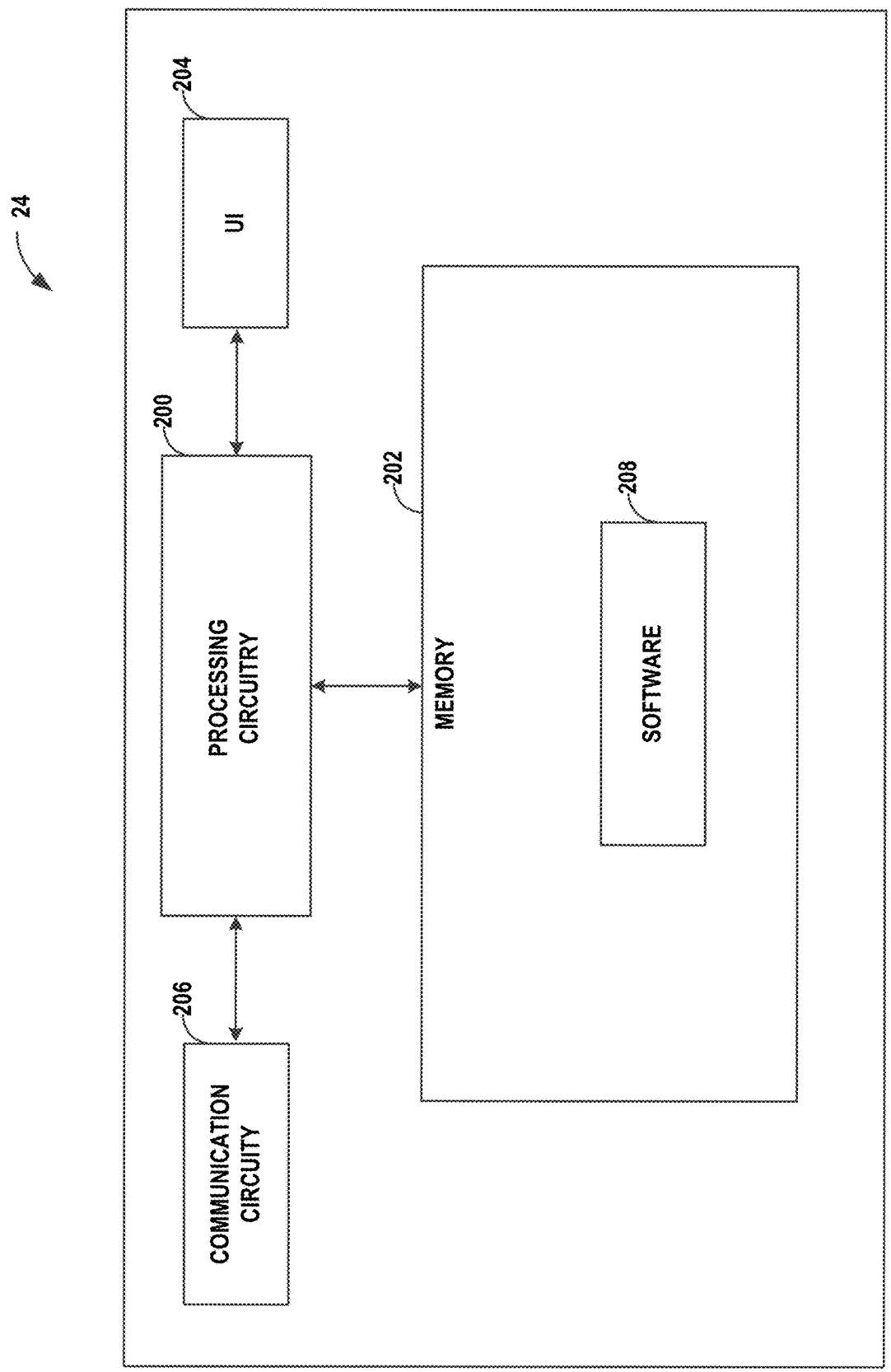
FIG. 4 is a block diagram of an example external device used with a medical device according to the techniques of this disclosure.

FIG. 4 is a functional block diagram illustrating an example of an external device 24 configured to communicate with sensor 20, receive information from sensor 20 and store and retrieve information from memory 19. In the example of FIG. 4, external device(s) 24 and/or 25 includes processing circuitry 200, memory 202, user interface (UI) 204, and communication circuitry 206. External device(s) 24 and/or 25 may be a dedicated hardware device(s) with dedicated software for reading sensor data. Alternatively, external device(s) 24 and/or 25 may be an off-the-shelf computing device, e.g., a desktop computer, a laptop computer, a tablet, or a smartphone running a mobile application enabling external device(s) 24 and/or 25 to read sensor data from sensor 20 and memory 19.

In some examples, a user of external device(s) 24 and/or 25 may be clinician, physician, intensivist, or heath care giver. In some examples, a user uses external device(s) 24 and/or 25 to monitor a patient's kidney function, e.g., based on information sensed by sensor 20 or otherwise derived from information sensed by sensor 20 in the manner described herein. In some examples, the user may interact with external device(s) 24 and/or 25 via UI 204, which may include a display to present a graphical user interface to the user, and a keypad or another mechanism (such as a touch sensitive screen) for receiving input from the user. External device(s) 24 and/or 25 may communicate with sensor 20 and/or memory 19 using wired, wireless or optical methods through communication circuitry 206.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, such as software 208, which may include one or more program modules, which are executable by processing circuitry 200. When executed by processing circuitry 200, such program instructions may cause processing circuitry 200 and external device 24 to provide the functionality ascribed to them herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Figure 5:
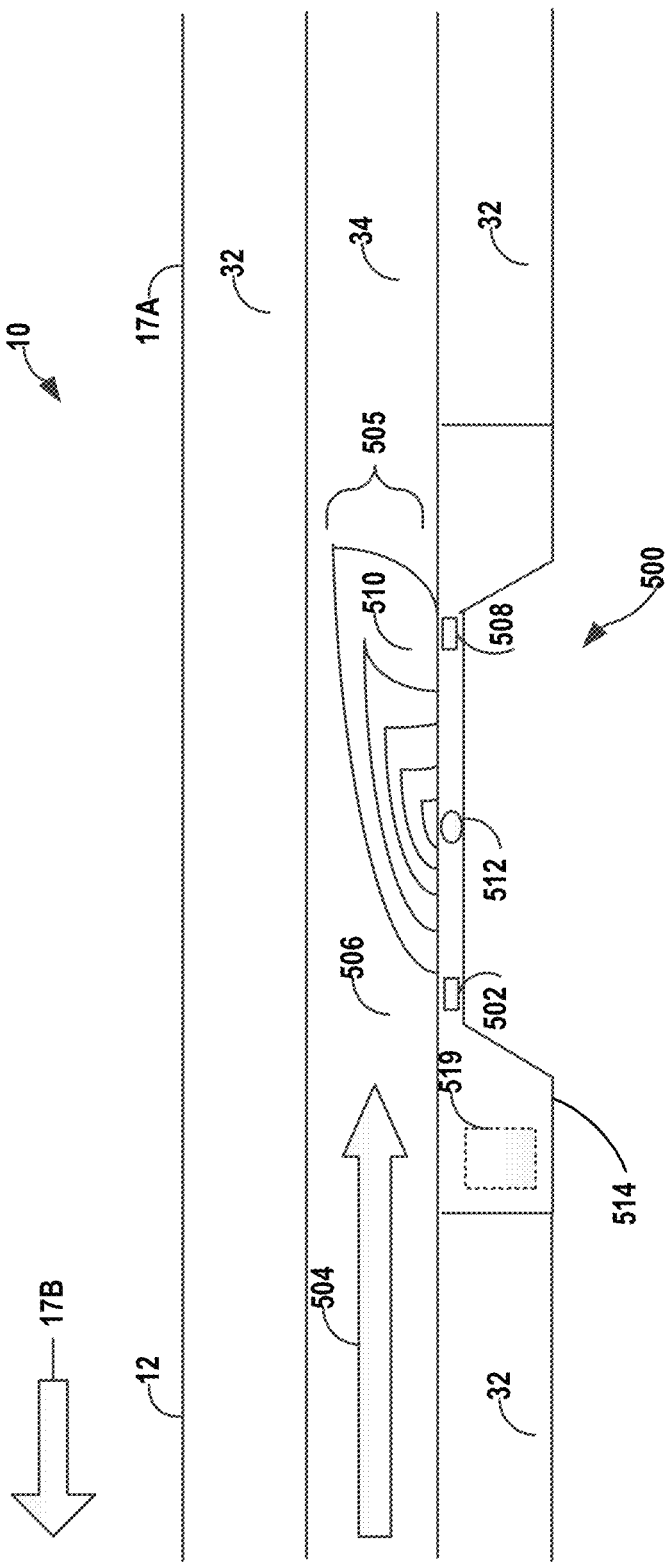
FIG. 5 is a diagram illustrating an example flow sensor used with a medical device according to the techniques of this disclosure.

FIG. 5 is a conceptual and schematic diagram illustrating an example of catheter 10 including example flow sensor 500 along a longitudinal cross-section according to an example of this disclosure. Flow sensor 500 may be an example of sensor 20 described with regard to FIG. 1. For ease of description, the example of FIG. 5 is described with regard to medical device 10 of FIG. 1. However, it is recognized that flow sensor 500 may be employed in any other type of medical device having a lumen through which a fluid flows to monitor the fluid in the manner described herein via sensor 500. For ease of illustration, lumen 36 is not shown in FIG. 5.

Sensor 500 is configured to sense the flow rate (e.g., in terms of velocity and/or volumetric flow rate) of fluid 504 within lumen 504 of elongated body 12. As shown, sensor 500 may include sensor body 514 having first temperature sensor 502, second temperature sensor 508 and heating member 512. In the example of FIG. 5, first temperature sensor 502 is located proximal to second temperature sensor 508 on elongated body 12 with heating member 512 being between first and second temperature sensors 502 and 508. In other examples, heating member 512 may be located proximal to first temperature sensor 502 and second temperature sensor 508, with first temperature sensor 502 being proximal to second temperature sensor 508. Sensor 500 may determine a parameter based on the sensed temperatures. Once the determination is made, processor 200 may control user interface 204 on external device 12 to present an indication of the determined value. For example, processor 200 may control user interface 204 of the external device to present an indication of a velocity and/or volumetric flow rate determine with flow sensor 500.

Sensor body 514 of flow sensor 500 may be attached to wall 32 of elongate body 12 so that first temperature sensor 502, second temperature sensor 508 and heating member 512 are adjacent to fluid 504 within lumen 34. In some examples, sensor body 514 may be releasably coupled to wall 32 of elongated body 12 defining lumen 34, e.g., so that sensor 500 may be detached from elongate body 12 and reused in another catheter such as medical device 10. Sensor body 514 may be releasably connected, e.g., mechanically with latches, snaps, threads, slides, cams, deformable elastic connections, and/or magnetically. Flow sensor 500 may be located on distal portion 17A of elongated body 12.

In operation, heating member 512 may be configured to heat fluid 504 flowing within lumen 34, e.g., via heat conducted from heating member 512 into fluid 504 at the location of heating member 512 on elongated body 12. The heat transferred from heating member 512 into fluid 504 may create temperature gradient 505. Temperature gradient 505 may be influenced by the flow of fluid 504 within lumen 34. To sense the flow rate of fluid 504, first temperature sensor 502 may sense a first temperature of a fluid 504 at a first location 506 in lumen 34. Second temperature sensor 508 may also sense a second temperature (e.g., within temperature gradients 505) of the fluid 504 at a second location 510 in lumen 34 that is downstream of first temperature sensor 502 and heating member 512. Sensor 500 may then determine the flow rate of fluid 504 based on the difference in the temperature of fluid 504 sensed by first temperature sensor 505 and second temperature sensor 508. For example, a greater the temperature difference between first temperature sensor 502 and second temperature sensor 508 indicates a lesser flow rate of fluid 504. For example, a large temperature difference may indicate a lower flow rate and the smaller the temperature difference may indicate a higher flow rate.

First temperature sensor 502, second temperature sensor 508 and heating member 512 may be located on the other surface of wall 32 of elongated body 12, embedded within wall 32 of elongated body 12, or positioned within lumen 34 defined by wall 34. In some examples, one or more of first temperature sensor 502, second temperature sensor 508 and/or heating member 512 may be located within lumen 34. While FIG. 5 shows sensor body 514 and associated components as being located as a discrete circumferential portion of elongated body 12, in some examples, sensor body 514 and/or one or more of the components may substantially surround lumen 34 of elongated body 12. For example, first temperature sensor 502, second temperature sensor 508 and/or heating member 512 may wrap around lumen 34 of elongated body 12.

First and second temperature sensors 502 and 508 may be any suitable sensor capable of sensing the temperature of fluid 504 within lumen 34 in the manner described herein. In some examples, temperature sensor 502 and 508 are thermocouple sensors or thermistor sensors. Temperature sensors 502 and 508 may be micro-electromechanical system (MEMS) sensors, such as MEMS thermocouples and/or thermistors.

Heating member 512 may be any heating device suitable for heating fluid 504 within lumen 34 in the manner described herein, e.g., in a manner that creates temperature gradient 505 in fluid 504 flowing within lumen 34. In some examples, heating member 512 may be an electrically resistive element, such as nichrome 80/20 (80% nickel, 20% chromium), Kanthal (FeCrAl), Cupronickel (CuNi), or other materials. Heating member 512 may heat fluid 504 as indicated by gradient layers 505 (including first and second locations 506 and 510) extending outward from heating member 512. Heating member 512 may be located adjacent to lumen 34 of elongated body 12, or within lumen 34.

Sensor body 514 may be comprised of most any material such as is common in printed circuit board design (e.g., FR-2 (phenolic cotton paper), FR-3 (cotton paper and epoxy), FR-4 (woven glass and epoxy), FR-5 (woven glass and epoxy), FR-6 (matte glass and polyester), G-10 (woven glass and epoxy), CEM-1 (cotton paper and epoxy), CEM-2 (cotton paper and epoxy)) In another example, sensor body may have a flexible design so it may contour to the cylindrical shape of elongated body 10, thus allowing sensors 502 and 508 and heating member 512 to be as close to elongated body 12 to ensure proper heat transfer and sensor measurements. Flexible PCB materials include PI (polyimide) film and PET (polyester) film apart from which polymer film is also available like PEN (polyethylene nphthalate), PTFE and Aramid etc. In an example, sensor body 514 may be over molded with silicone, thermoplastic, or other material.

Sensor 500 may require calibration information to be accurate. Sensor 500 may require sensor-specific calibration information to produce an accurate measurement and compensate for variability in sensor 500. Sensor 500 may store this calibration information on memory 519 on sensor 20. External device 24 may use this calibration information to more accurately read sensor data being sent from sensor 500. In another example, memory 19 may store sensor calibration information to calibrate sensor 500 based on the sensor calibration information stored by memory 19.

Temperature sensors 502 and 508, heating member 512 and sensor body 514 may all be separate components, or they may all be part of the same body, such as, all components being a part of sensor body 514 or all part of elongated body 12. Each of temperature sensors 502 and 508, heating member 512 and sensor body 514 may be integral with elongated body 12 or each component may be coupled to elongated body 12 together on sensor body 514 or separately.

First temperature sensor 502, second temperature sensor 508, and heating member 512 may have any suitable spatial arrangement on elongated body 12. In some examples, heating member 512 is located proximal to both first temperature sensor 502 and second temperature sensor 508 on elongated body 12. In other examples, heating member 512 is between first temperature sensor 502 and second temperature sensor 508, with first temperature sensor 502 being located proximal to heating member 512 on elongate body 12. In some examples, temperature sensors 502 and 508 may be about 2 mm to about 20 mm apart from each other on elongated body 12 although other values are contemplated. The distance between first and second temperature sensors 502 and 508 may be selected such that there is at least some thermal decay in the fluid (temperature change) between the locations of first and second temperatures sensors 502 when fluid 504 is flowing at flow rates of interest.

In some examples, the distance between temperature sensors 502 and 508 may be predetermined and/or stored in memory 519, memory 202 or memory 19. In some examples, the distance between temperature sensors 502 and 508 may constitute sensor calibration data that is used by processing circuitry 200 or other processing circuitry to calibrate sensor 500. In some examples, sensor 500 may include memory 519 that stores such calibration data for calibration of sensor 500, e.g., in cases in which sensor 500 is removably coupled to elongated body 12 so that sensor 500 may be calibrated and used on multiple different catheters.

As described above, first temperature sensor 502 may be located proximal of heater member 512 on elongated body 12. In some examples, first temperature sensor 502 is located at a proximal position on elongated body 12 relative to heating member 512 where the temperature of fluid 504 is not substantially changed by heater member 512 when heating member 512 heats fluid 504. In other examples, first temperature sensor 502 is located at a proximal position on elongated body 12 relative to heating member 512 where the temperature of fluid 504 is influenced (e.g., changed) by heating member 512 when heating member 512 heats fluid 504 (e.g., first temperature sensor 502 senses the temperature of fluid 504 within temperature gradient 505). In some examples, first temperature sensor 502 may be located distal to heating member 512 at a location where the temperature of fluid 504 is influenced by heating member 512 when heating member 512 heats fluid 504. In some examples first temperature sensor 502 may be located downstream or distal of second temperature sensor 508 where the heat transferred by heating member 512 has dissipated and fluid 504 is assumed to be near room temperature.

Second temperature sensor 508 may be located distal to both first temperature sensor 502 and heating member 512, and may be at a position on elongated body 12 within temperature gradient 505, e.g., as compared to a location at which the temperature of fluid 504 is not changed by heating member 512 when fluid 504 is heated. In some examples, when fluid 504 is not flowing in lumen 34, second temperature sensor 508 may measure a temperature at second location 510 which is substantially the same as the temperature of fluid 504 directly adjacent to heater member 512. The flow rate of fluid 504 may change the temperature difference between first and second sensors 502 and 508, e.g., where a change in flow rate of fluid 504 results in a change in the temperature difference of fluid 504 sensed at first location 506 and second location 510 by temperatures sensors 502 and 508, respectively.

Figure 6:
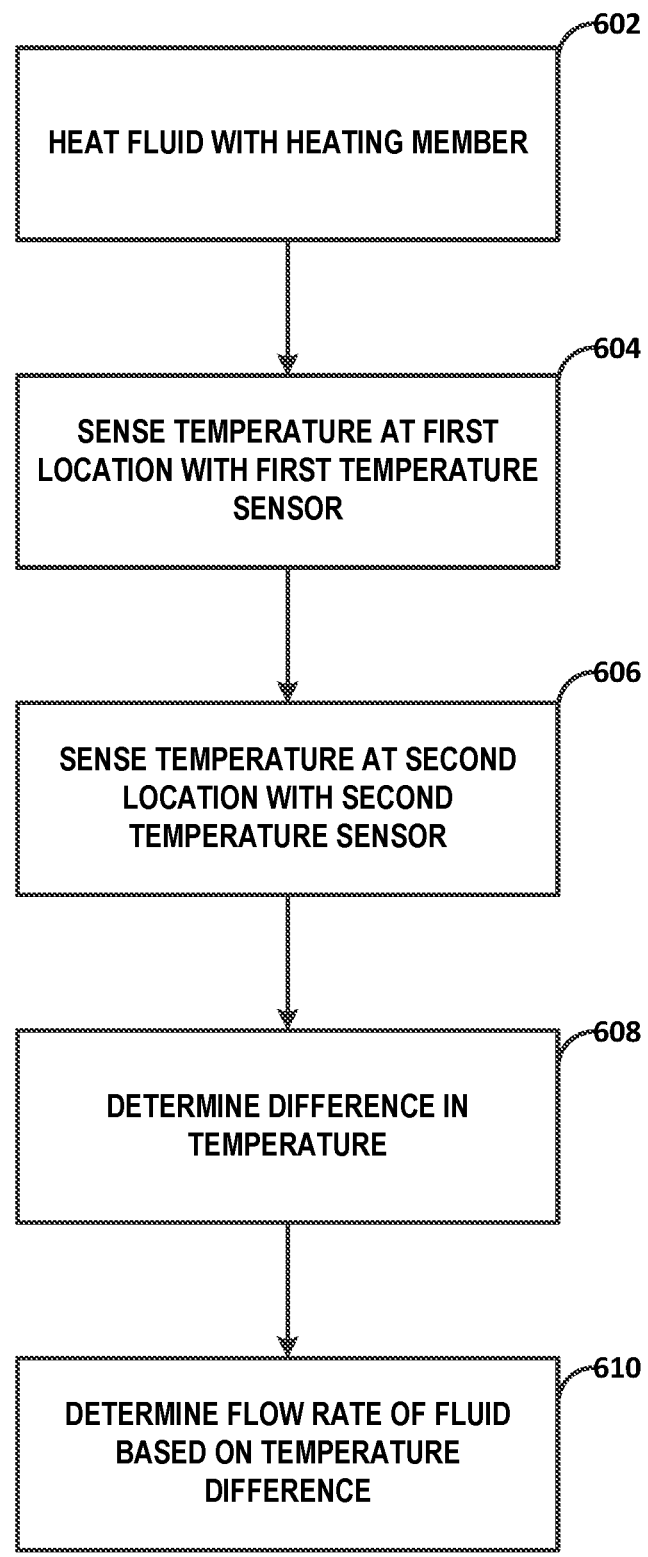
FIG. 6 is a flow diagram illustrating an example technique for monitoring or otherwise sensing a flow rate of fluid within a lumen using the sensor of FIG. 5 according to the techniques of this disclosure.

FIG. 6 is a flow diagram illustrating an example technique for monitoring or otherwise sensing a flow rate of fluid 504 within lumen 34 using sensor 500. Processor circuitry 200 may be used to calculate a flow rate determination of fluid 504 and the technique of FIG. 6 will be described as such for ease of description. However, processing circuitry on medical device 10, elongated body 12, and/or other device may be used to make the flow rate determination.

As shown in FIG. 6, heating member 512 may heat fluid 504, e.g., as fluid 504 flows from proximal end 17B to distal end 17A of elongated body 12 within lumen 34 heating member (602). In some examples, a user may begin a monitoring process at external device 24. Upon initiation of a monitoring process at external device 24, processing circuitry 200 may initiate the sensing process for flow sensor 500. This may include providing power to heating member 512 to begin heating fluid 504. This may include external device 24 requesting a verification through user interface 204 fluid 504 is currently flowing through lumen 34. In another example, processing circuitry 200 may not apply power to heating member 512 until fluid 504 is within lumen 34. Thus, heating member 512 is not applying heat directly to lumen 34 without any fluid 504 to dissipate the heat and possibly cause melting of lumen 34. Processing circuitry 200 may also supply power to first temperature sensor 502 and second temperature sensor 508 (e.g., if temperature sensor 502 and temperature sensor 508 require a power source). In some examples, flow sensor 500 may have a power switch and an onboard power supply to power heating member 512. A user may power on the flow sensor 500 when the flow sensing process begins or when fluid 504 begins flowing through lumen 34.

Heat transferred from heating member 512 to fluid 504, indirectly or directly, may heat fluid 504 adjacent to heating member 512 to generate temperature gradient 505 within fluid flow 504. In some examples, heating member 512 may increase the temperature of fluid 504 at least 0.01 degrees Celsius, such as a maximum temperature increase of about 0.01° C. to about 5° C. within lumen 34. Heating member 512 may operate substantially continuously to generate gradient 505 within fluid 504 (e.g., to allow for substantially continuous monitoring of the flow rate of fluid 504) or periodically (e.g., to allow for periodic sampling of the flow rate of fluid 504).

First temperature sensor 502 at first location 506 may sense a first temperature of fluid 504, e.g., while heating member 512 is heating fluid 504 or shortly thereafter (604). As described above, depending on the location of first temperature sensor 502 relative to heating member 512, the temperature of fluid 504 may or may not be changed by the heating of fluid 504 via heating member 512. Second temperature sensor 518, located at second location 510, may sense a second temperature of fluid 504, e.g., while heating member 512 is heating fluid 504 or shortly thereafter (606). The temperature of fluid 504 at second location 510 may be increased by the heat transferred to fluid 504 via heating member 504. As described herein, as a result of the flow of fluid 504 within lumen 34, there may be a temperature difference of fluid 504 between first location 506 and second location 510. This temperature difference may change based on the flow rate of fluid 504 and, thus, allows sensor 500 to sense the flow rate of fluid 504 (e.g., in terms of a flow rate value and/or change in flow rate over a period of time).

Processing circuitry 200 may determine the difference in the first temperature of fluid 504 sensed by first temperature sensor 502 and the second temperature of fluid 504 sensor by second temperature sensor 508 (608). Processing circuitry 200 may then determine a flow rate of fluid 504 based on the difference in temperature between first sensed temperature and the second sensed temperature (610). For example, processing circuitry 200 may determine a flow rate value that corresponds to the determined temperature difference (e.g., based on preprogrammed values stored in a lookup table or other data structure, or a preprogrammed modeling on the fluid flow within lumen 34) and/or may identify trends over time with or without regard to the actual flow rate value (e.g., by identifying changes in temperature difference that correspond to an increase or decrease in flow rate over the period of time). Processing circuitry 200 may be configured to sample the temperature difference substantially continuously or periodically (e.g., based on a preprogrammed schedule or input from a user indicating that a flow rate of fluid 504 should be determined). Processing circuitry 200 may determine a correlation between the change in temperature of fluid 504 through sensor 500 and the flow rate may depend on many variables which may be considered with calibration information stored on memory 519, memory 19 and/or memory 202. The calibration information may include manufacturing variances and tolerances of sensor 500. The calibration information may also include the dimensions of lumen 34, the exact position of first temperature sensor 502 and second temperature sensor 508 and heating member 512, as well as the constitution of fluid 504, such as bubbles, thermal conductivity, thermal capacity. Values like the unique characteristics of first temperature sensor 502 and second temperature sensor 508 and lumen 34 may be measured during manufacturing. In some examples, the constitution of fluid 504 may be assumed unless otherwise measured.

In some examples, processing circuitry 200 may control user interface 204 to display the determined flow rate to a user (e.g., operator, clinician, intensivist, surgeon or physician) to observe. Further, as will be described below, processing circuitry 200 may use the flow rate to calculate density, urine output, and/or other parameter of fluid 504 and display these parameters to the user. In some examples, processing circuitry may generate an alarm displayed via user interface 204, sound an alarm audibly through a speaker (not shown in FIG. 4) or utilize another user interface based on a determination that the flow rate has changed more or less than a threshold amount (e.g., when the increase or decrease is indicative of impaired kidney function or increased risk of AKI). In another example, processing circuitry may determine there is no flow (e.g., such as no temperature difference between first temperature sensor 502 and second temperature sensor 508) or even a back flow condition where the sensed temperature at first temperature sensor 502 is greater than the temperature at the second temperature sensor 508.

Flow sensor 500 may be used to measure flow rates in the range of nanoliters to microliters per minute although other values are contemplated. Processing circuitry 200 may use any suitable processing technique to determine the flow rate based on the temperature difference. Processing circuitry 200 may determine a total flow volume utilizing a flow rate, known dimensions of lumen 34 and a change in time during a procedure. Memory 202 (FIG. 4) may store software 208, an algorithm or a lookup table of the fluid's constitution (e.g., specific heat, density, specific gravity, etc.) that processing circuitry may use to determine various parameters of fluid 504. In another example, an operator may enter specific fluid types before use of medical device 10 or memory 202 may have come preloaded with values for fluids based on the targeted use of medical device 10 (e.g., urine in the case of a urinary catheter such as a Foley catheter). In another example, flow sensor 500 may have onboard processing circuitry that may correlate a flow rate based on sensor data collected from first temperature sensor 502, second temperature sensor 508 and heating member 512. For example, processing circuitry 200 may determine a temperature difference of "X". Processing circuitry 200 may access a lookup table, stored in memory 202, defined for a particular diameter lumen, the fluid within the lumen and determine the flow rate corresponding to the measured temperature difference X. In another example, an algorithm or software 208 may model the flow within the system specific to diameter 35, fluid heat capacity and/or the like and use temperature difference as an input that generates a flow rate output.

In one example, external device 24 receives temperature data from temperature sensors 508 and 502 for use in a thermal dilution algorithm to determine a flow rate of fluid 504. Heating member 512 may have first and second temperature sensor 502 and 508 on either side of heating member 512. Heating member 512 may heat fluid 504 and first and second temperature sensors 502 and 508 record the temperature of fluid 504 both upstream by first temperature sensor 502 and downstream of heater member 512 by second temperature sensor 508. The greater the difference in temperature, the slower the flow rate of fluid 504 and the lesser the difference in temperature, the faster the flow rate of fluid 504. In some examples, memory 519 may contain calibration data that processing circuitry 200 or another processing circuitry may reference to obtain a more accurate information regarding the lumen diameter, thermal characteristics of fluid 504 and temperature difference.

Figure 7A:
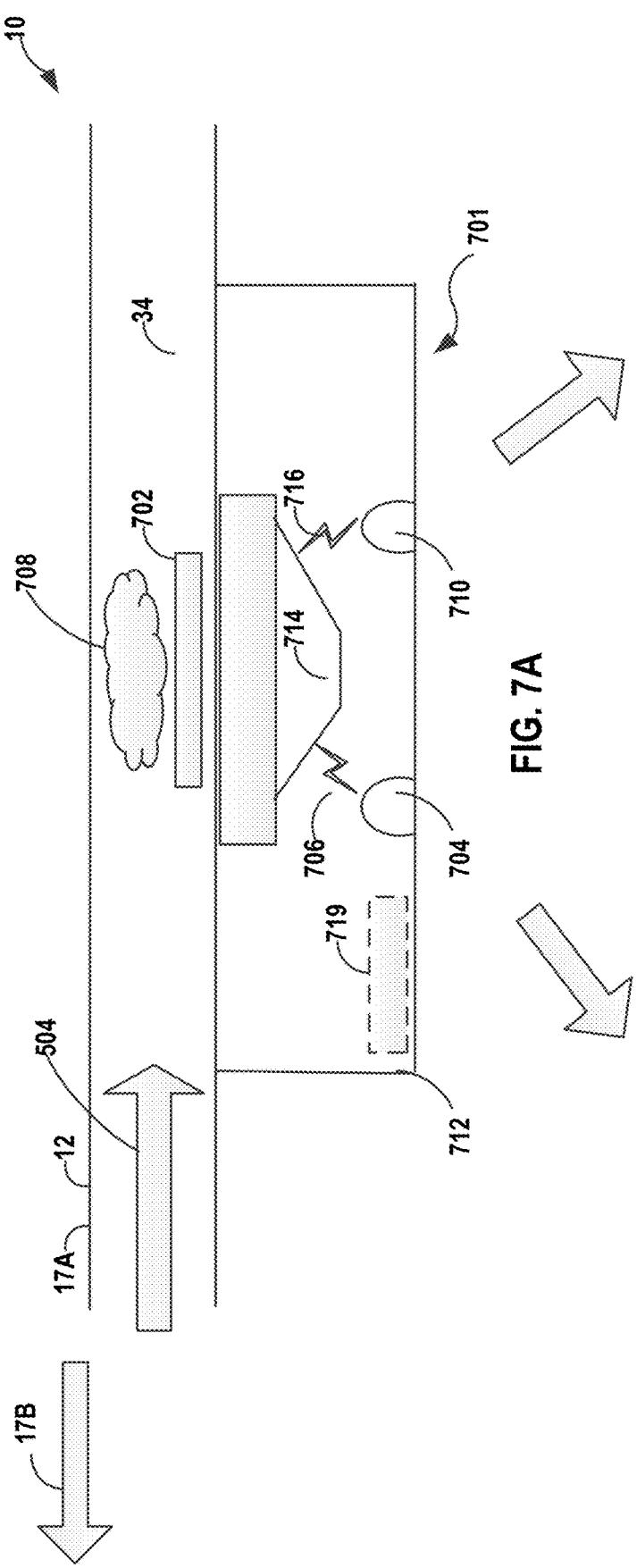
FIG. 7A is a diagram illustrating an example oxygen sensor used with a medical device according to the techniques of this disclosure.

In some examples, the determined instantaneous volumetric flow rate may be determined over time to determine a total volumetric flow per unit of time or total fluid output. This measurement may be very useful to clinicians and may be expressed in ml/min or ml/hour and sometimes normalized to a patient's weight to ml/hr/kg FIG. 7A is a diagram illustrating an example oxygen sensor 701 used with a medical device 10 according to the techniques of this disclosure. Oxygen sensor 701 may be an example of sensor 20 of medical device 10 (FIG. 1), may be used in place of sensor 20, used in combination with sensor 20 or sensor 500 or in addition to sensor 20 and sensor 500.

Oxygen sensor 701 may be configured to determine an oxygen level within fluid 504 utilizing, e.g., a fluorescence lifetime technique (FLT). Oxygen sensor 701 includes sensor body 712 housing a light source 704, a light detector 710, an optional lens 714 and a fluorescence material 702. Sensory body 712 may support light source 704, light detector 710 and optional lens 714. Sensor 701 may determine a parameter based on the sensed fluorescence. Once the determination is made, processor 200 may control user interface 204 on external device 12 to present an indication of the determined value. For example, processor 200 may control user interface 204 of the external device to present an indication of oxygen saturation of fluid 504 determined with oxygen sensor 701.

In one example, sensor 701 is configured to sense oxygen in fluid 504 (e.g., oxygen concentration) using a FLT. In this technique, fluorescence material 702 is exposed to light 706 (which may be a specific wavelength) emitted from light source 704. Fluorescence material 702 (referred to as a fluorescence lifetime material or an optrode), glows (fluoresces 708) when exposed to this light. In specific materials used for fluorescence material 702, the rate at which the glow fades is inversely proportional to the amount of oxygen it is exposed to. In these materials, the more oxygen is present the faster the glow fades. By measuring the rate of glow decay in calibrated optrodes with light detector 710, sensor 701 may measure the amount of oxygen in fluid 504, e.g., accurately and/or substantially continuously.

Figure 7B:
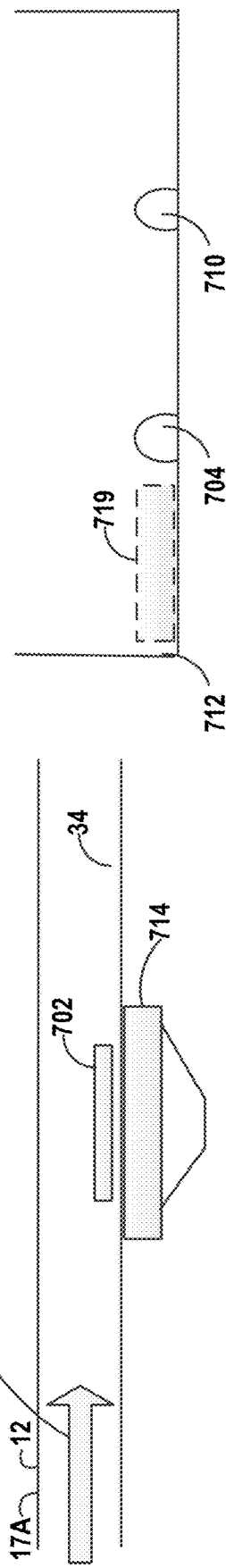
FIG. 7B is a diagram illustrating the example oxygen sensor of FIG. 7A separated into a disposable portion and a reusable portion according to techniques of this disclosure.

For use in a Foley catheter or other catheter, in some examples, fluorescence material 702 may needs relatively small, e.g., to fit within lumen 34 without substantially obstructing the flow for fluid 504. The fluoresces of the fluorescence material 702 may not be very intense and therefore light detector 710 (referred to in some examples as a photodiode) may needs to be relatively high-performance, which may be expensive and large. To overcome these limitations, in some examples, fluorescence material 702 may be disposable and within the drainage lumen 34 of the Foley catheter or other catheter, but the light source 704 and light detector 710 may be reusable and detachably coupled to elongated body 12. In addition, option lens 714 may be configured to gathers the fluorescence 708 from fluorescence material 702 and focusses light 716 on light detector 710 to increase its intensity and/or reduce the performance requirement of light detector 710. In some examples, lens 714 may additionally, or alternatively, focus the excitation light 706 emitted from the light source 704. As illustrated in FIG. 7B, in some examples, lens 714 may be a part of the disposable portion of sensor 701. Alternatively, lens 714 may be on the re-usable portion of sensor 701 (e.g., in addition to light source 704 and/or light detector 710). As described below, lens 714 may have one or more filters to improve the delivery of the excitation light 706 from light source 704 and/or sensing of the fluorescent light 716 by light detector 710. In other examples, sensor 701 does not include lens 714.

As described herein, oxygen sensor 701 may be an optical sensor device that optically measures a specific substance (e.g., oxygen in fluid 504) with the aid of a fluorescence material 702 (which may be referred to as an optode or optrode). For FLT, e.g., oxygen sensor 701 may utilize luminescence (e.g., fluorescence and phosphorescence) or chemiluminescence to measure the oxygen within fluid 504 within lumen 34. However, other methods of optical measurement may be used. In some examples, optical sensing techniques such as reflection, absorption, evanescent wave, surface plasmon resonance, may be used.

Fluorescence material 702 may be any suitable material configured to fluoresce in response to being exposed to light 716 from light source 704 in the manner described herein. In some examples, fluorescence material 702 may include, e.g., platinum octaethylporphyrin (PtOEP), phosphors such as palladium (Pd)-porphyrin, PdTPTBP/PtTPTBP (palladium (ii)/platinum(ii) tetraphenyltetrabenzoporphyrin); Ir(Cs)$_2$acac (iridium(iii) bis-(benzothiazol-2-yl)-7-(diethyl-amino)-coumarin-(acetylacetonate)); and/or Ru-dpp (ruthenium(ii) tris-4,7-diphenyl-1,10-phenanthroline), white phosphorus, nitric oxide, fluorophores and fluorophore derivatives, such as of rhodamine, coumarin and cyanine. When exposed to excitation light 506, fluorescence material 702 releases fluorescence 708. Fluorescence 708 of fluorescence material 702 may be quenched, or caused to dissipate, by specific analytes oxygen) in fluid 704. The fluorescence 708 to oxygen ratio within fluid 504 may not be linear. Oxygen sensor 701 may have a greater sensitivity at low oxygen concentration, (e.g., when the fluorescence 708 is the greatest) then at high oxygen concentration (e.g., when the fluorescence 708 is the lowest). Nevertheless, oxygen sensor 701 may operate in a region of 0-100% oxygen saturation in fluids containing mostly water, such as urine, with a calibration for the type of material reacting with fluorescence material 702.

Light source 704 may be any suitable light device configured to emit light 706 in the manner described herein. In some examples, light source 704 includes an LED (light emitting diode), amplified natural lighting, HID (high-intensity discharge) and/or fluorescent and incandescent source capable of emitting light 706, e.g., at an excitation wavelength. Light source 704 emits a wavelength of light which excites the fluorescence material 702. The wavelength of light may be different for differing fluorescence material 702 (e.g., different fluorescence material chemistries have different excitation frequencies). Light source 704 may be powered by an onboard power source on oxygen sensor 701 or maybe powered by external device 24 providing power through connection 38 (FIG. 2). In some examples, light source 704 may emit a specific wavelength of light, that causes fluorescence material 702 to enter an excited state. FLT may be the time fluorescence material 702 spends in the excited state ($T_{es}$). In some examples, the FLT may vary from picoseconds to hundreds of nanoseconds depending on fluorescence material 702. FLT may not depend on fluorescence concentration, absorption by fluid 504, thickness of fluid 504, method of measurement, fluorescence intensity, photo-bleaching and/or excitation intensity. However, FLT may be affected by external factors, such as temperature (discussed below, which may be calibrated for), polarity, and the presence of fluorescence quenchers (e.g., oxygen).

Light detector 710 may be any type of light detector configured to detect fluoresced light 716 from material 702, e.g., to detect the decay of light 716 from material 702 over a period of time. In some examples, light detector 710 may be a photodiode (e.g., PN photodiodes, PIN photodiodes, avalanche photodiodes (particularly well suited for fluorescence sensor due to their high sensitivity), and Schottky photodiodes), photoconductor (e.g., photoresistor), photovoltaic device (e.g., photocell), phototransistor, and/or photodiode. Light detector 710 may detect light excitation between 300 nm and 800 nm. Light detector 710 may detect the light excitation of fluorescence 708. In some examples, processing circuitry 200 may process the light excitation data of light detector 710 to detect the time fluorescence 708 spends in the excited state or otherwise detect the rate of decay of fluorescence 708.

Lens 714 may be configured to focus light 706 emitted from light source 704 to fluorescence material 702 and/or focus fluorescence 708 to light detector 710 (as represented by light 716). In some examples, lens 714 may be optical glass, crystals, plastics, mirrors or other material that focuses light in the manner described herein. Lens 714 may focus fluorescent light 716 on light detector 710 to increase its intensity and reduce the performance requirement of light detector 710. Lens 714 may also focus light 706 from light source 704 onto fluorescence 708. Lens 714 may be configured to be disposable or re-usable as part of sensor 701. In some examples, lens 714 may also have filters to optimize the delivery of excitation light 706 or sensing of fluorescence light 716. With filters, light source 704 and light detector may not need to be so precise and thus less expensive alternatives for light source 704 and light detector 710 may be used. By filtering excitation light 706 being emitted onto fluorescence 708 and filtering fluorescence light 716 being detected by light detector 710, both light source 704 and light detector 710 may not necessarily need to be very high performing devices and thus may be less expensive.

Sensor body 712 may be configured to house, support or otherwise couple together one or more of light source 704, light detector 710, or lens 714, e.g., in a desired arrangement. In some examples, sensor body 712 may be configured to be removably coupled to elongated body 12, e.g., to allow for a portion of sensor 701 to be reusable with other catheters (e.g., as shown in FIG. 7B).

In some examples, sensor body 712 may include a material that is used imprinted circuit board design (e.g FR-2 (phenolic cotton paper), FR-3 (cotton paper and epoxy). FR-4 (woven glass and epoxy), FR-5 (woven glass and epoxy), FR-6 (matte glass and polyester), G-10 (woven glass and epoxy), CEM-1. (cotton paper and epoxy), CEM-2 (cotton paper and epoxy)). In another example, sensor body 712 may have a flexible design so it may contour to the cylindrical shape of elongated body 12, thus allowing lens 714, light source 704 and light detector 710 to be as close to elongated body 12 as possible to ensure reliable light transfer and sensor measurements. Flexible PCB materials include PI (polyimide) film and PET (polyester) film apart from which polymer film is also available like PEN (polyethylene nphthalate), PTFE and Aramid etc.

Sensor 701 may require calibration information to be accurate. Sensor 701 may require sensor-specific calibration information to produce an accurate measurement and compensate for variability in sensor 701. Sensor 701 have memory 719 on sensor 701 that stores sensor calibration information that is used by external device 24 to more accurately read sensor data being sent from sensor 701. In another example, memory 19 may store sensor calibration information to calibrate sensor 701 based on the sensor calibration information stored by memory 19.

In FLT, fluorescence material 702 may be located within lumen 34 with fluid 504 on an opposite side of lumen 34 from lens 714, light source 704 and light detector 710. Medical device 10 may come with fluorescence material 702 within lumen 34 or fluorescence material 702 may be inserted in a separate procedure before use of medical device 10. When powered on, by processing circuitry 200 or a separate power source onboard (not shown) light source 704 may emit light 706, e.g., at a specific wavelength to expose fluorescence material 708 to emitted light 706. Light source 704 may emit light 706 through elongated body 12. In some examples, elongated body 12 is transparent to emitted light 706 or otherwise configured to allow light 706 to be transmitted through elongated body 12 to fluorescence material 702.

Fluorescence material 702 within fluid 504, as discussed above, may be configured to fluoresce 708 when exposed to light 706 in lumen 34. Light detector 710 may detect fluorescence 708 of fluorescence material 702. Processing circuitry 220 may then determine the amount of oxygen within fluid 504 by recording the time for fluorescence 708 ($T_f$) to quench (or dissipate) or otherwise decay. Processing circuitry 200 may then determine the time to dissipate ($T_f$) with ($T_{es}$) and based upon this difference, determine how much oxygen is present within fluid 504. Further, processing circuitry such as processing circuitry 200 may calibrate for the temperature of fluid 504, which may have an effect on how quickly fluorescence 708 dissipates.

In another example, fluorescence material 702 may be excited with light pulses (e.g., light initiated in a sine wave pulse). Processing circuitry 200 may then determine a frequency shift of the fluorescence material response that measures the fluorescence decay time continuously. In another example, when fluorescence material 702 is excited the fluorescence saturation time may be measured and determined by processing circuitry 200, where the saturation time is proportional to oxygen content.

In some examples, light source 704 and light detector 710 are releasably coupled to elongated body 12, e.g., either separate from each other or together via the detachment of sensor body 712 from elongated body 12 as shown in FIG. 7B. In other examples, each of light source 704 and light detector 710 may be part of or integral with elongated body 12 or may be separate and coupled to elongated body 12 for use during a procedure. In some examples, sensor body 712 may be releasably coupled to elongated body 12 as shown in FIG. 7B where sensor body 712 may support light source 704 and light detector 710. In some examples, sensor body 712 may be part of or integral with elongated body 12. In some examples, lens 714 may be added if necessary, for improved performance of light source 704 and light detector 710 and may be placed on elongated body 12 in between fluorescence material 702 and light source 704. Lens 714 may be used to focus light 706 to fluorescence material 702 in lumen 34. Lens 714 may focus fluorescence 708 from fluorescence material 702 to light detector 710. In some examples, lens 714 may be disposed of along with elongated body 12 and fluorescence material 702 when the patient no longer needs medical device 10.

Processing circuitry 200 may use time for fluorescence 708 ($T_f$) to determine an amount of oxygen within fluid 504 within lumen 34. As discussed, fluorescence 708 has an excitation limit ($T_{es}$) which exists outside of factors which may shorten this time period. One of these factors is the amount of oxygen present within fluorescence 708. Oxygen will cause fluorescence 708 to decay or quench faster than normal. Fluorescence 708 excitation time ($T_f$) may be at a maximum when there is no oxygen present. Thus, when no oxygen is present fluorescence time ($T_f$) equals or is substantially close to fluorescence excitation time ($T_{es}$) with all other variable the same (e.g., such as temperature). When an oxygen is present in fluid 504 and collides with fluorescence 708, this quenches the fluorescence 708. If fluid 504 has no oxygen present, then fluorescence time ($T_f$) should be close to or equal to the excitation state time ($T_{es}$). On the other hand, if fluid 504 has a 100% oxygen saturation, then fluorescence time ($T_f$) should be zero or substantially zero. As stated above, the relation to fluorescence time ($T_f$) and oxygen concentration may be non-linear. Therefore, processing circuitry 200 may use an algorithm to determine the amount of oxygen within fluid 504. In another example, processing circuitry 200 may utilize a lookup table stored on member 202 or memory 719, memory 19, where an oxygen content of fluid 504 is dependent on fluorescence time ($T_f$) and the temperature of fluid 504 (e.g., discussed above, temperature also affect fluorescence time).

For use with medical device 10, oxygen sensor 701 may be relatively small (e.g., 0.25 mm×0.25 mm and as large as 20 mm×20 mm). Fluorescence 708 may not be very intense and therefore light detector 710 may be a high-performance light detector 710. High-performance light detectors may be expensive and large. Thus, light source 704 may be reusable and light detector 710 may be reusable and may be located on a sensor body 712 and removed from elongated body 12 when a procedure is complete.

In another example, lens 714 may be used to focus fluorescent light 716 on light detector 710 to increase light intensity and reduce the performance requirement and thus cost of light detector 710. Lens 714 may also focus light 706 from light source 704 onto fluorescent material 702. Lens 714 may be part of disposable elongated body 12 of medical device 10, but it may also be located on sensor body 712. In another example, lens 714 may also have filters which filter out all light except the specific wavelength of excitation light 706. Further, the filters may filter wavelengths of fluorescent light 716 so only fluorescent light 716 is reflected onto light detector 710. Lens 714 may make it possible to use less expensive light sources 704 and light detectors 710. Thus, in some examples, light sources 704, light detectors and lens 714 may be disposable after use.

As discussed above, the accuracy of oxygen sensor 701 may be temperature dependent as temperature affects the fluorescence time ($T_f$). Thus, to provide accurate sensor readings, sensor 701 may be calibrated, e.g., in real time, to obtain an accurate oxygen measurement. To obtain this measurement the temperature of fluid 504 may need to be known. Therefore, the more accurately the temperature of fluid 504 is known, the more accurate a reading of oxygen can be obtained from sensor 701.

In an example of the present disclosure, a temperature reading may be obtained from sensor 500 (FIG. 5), memory 719, memory circuitry 19, memory 202 or another suitable component, and used to calibrate sensor 701. For instances when elongated body includes both sensor 500 (FIG. 5) and sensor 701, the temperature of fluid 504 may be determined via first temperature sensor 502 and/or second temperature sensor 508. In configurations in which sensor 701 is upstream/proximal of sensor 500, e.g., first temperature sensor 502 may be used as the reference for the temperature of fluid 504. In configurations in which sensor 701 is downstream/distal of sensor 500, second temperature sensor 508 may be used as the reference for the temperature of fluid 504. In other examples, first temperature sensor 502 or second temperature sensor 508 may be used to determine the temperature of fluid 504 within lumen 34 regardless of the location of sensor 701 for use in calibrating the oxygen sensing carried out by sensor 701. Further, flow sensor 500 may assist in a better understanding of the dissolved oxygen measurement of sensor 701. In an example, a low volumetric flow rate may mean the dissolved oxygen measurement of sensor 701 may not be as accurate to renal oxygenation due to the effects of the ureter, bladder, and slow transit time through lumen 34. Thus, an alert may be sent to user interface 204, providing an indication the sensed oxygen may be inaccurate due to low volumetric flow.

Processing circuitry 200 may use the temperature data collected from temperature sensor 502, temperature sensor 508, an estimated temperature based on a patient's body temperature, another sensor coupled to external device 24 or a temperature inputted by a user at user interface 204. Processing circuitry 200 may use the temperature to input into, e.g., an algorithm or a look up table to calibrate the oxygen calculation based on temperature of fluid 504 in combination with the rate of fluorescence decay detected by light detector 710.

Figure 8:
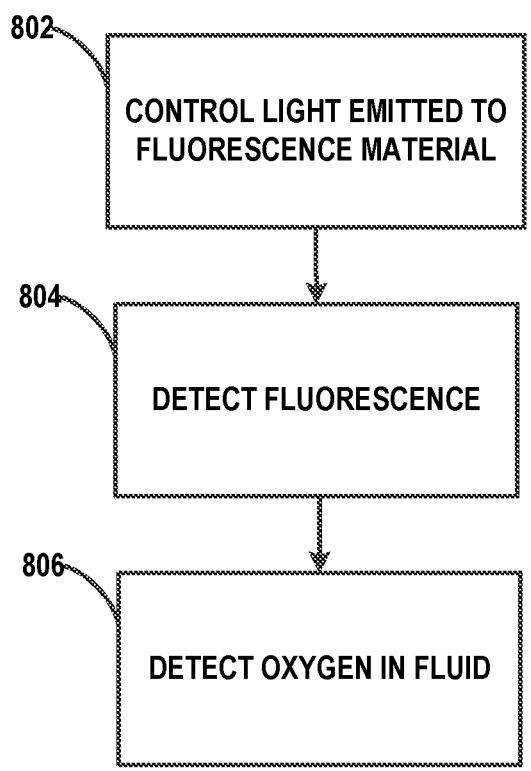
FIG. 8 is a flow diagram illustrating an example technique for monitoring or otherwise sensing oxygen within a fluid using the sensor of FIG. 7A according to techniques of this disclosure.

FIG. 8 is a flow diagram illustrating an example technique for monitoring or otherwise sensing oxygen within a fluid using sensor 701 of FIG. 7A according to techniques of this disclosure. Processing circuitry 200 may control light source 704 to emit light 706 to expose fluorescence material 702 within fluid 504 to light 706 in lumen 34 (802). In some examples, oxygen sensor 701 may be a stand-alone sensor having its own processing circuitry to control light source 704 to emit light 706 onto fluorescence 708 that is emitted from fluorescence material 702 when contacted by fluid 504 in lumen 34.

As discussed above, light source 704 may be powered by external device 12 through connection 38 or light source 704 may be powered by a power source (not shown in FIG. 7A or 7B) onboard oxygen sensor 701. Light source 704 is shown outside of elongated body 12 and emitting light 706 through elongated body 12 into lumen 34. In some examples, where elongated body is made of an opaque material, light source 704 may be embedded within elongated body 12 and closer to lumen 34 to help light source 704 emit light 706 into lumen 34. In some examples, oxygen sensor 701 may use a light source 704 emitting light 706 at wavelengths capable of penetrating material oblique to other wavelengths of light. In other examples, light source 704 may be located within or partially within lumen 34 so light 706 may contact fluorescence 708.

Light detector 710 may be located outside of elongated body 12 as shown in FIGS. 7A & 7B. In other examples, such as where elongated body 12 has an opaque material, light detector 710 may be located within or partially within elongated body 12 so light detector 10 may receiving fluorescence 716. In some examples, light source 704 and light detector may be embedded within elongated body 12 where light source 704 and light detector 710 may be placed closer to lumen 34, but still not within lumen 34 to allow for better emitting of light 706 and detection of fluorescence light 716.

Light detector 710 may detect fluorescence 708 of fluorescence material 702 (804). Based on detected FLT ($T_f$), processing circuitry 200 may determine an amount oxygen in fluid 504 within lumen 34. The greater the amount of oxygen present the lower the amount of fluorescence 708 detected and the lower the amount oxygen the higher the amount of fluorescence 708 detected. For example, in some instances, processing circuitry 200 may determine a concentration of oxygen in fluid 504. Processing circuitry 200 may continually monitor light detector 710 sensing the FLT ($T_f$). Based upon $T_f$ processing circuitry may utilize a lookup table or an algorithm to determine an oxygen level within lumen 34. Further, processing circuitry 200 may determine an oxygen level at a specific point in time, or a running average of oxygen amount or even determine a trend of oxygen with lumen 34 over time.

In some examples, lens 714 may focus emitted light 706 through lens 714, e.g., to fluorescence material 702. Additionally, or alternatively, lens 714 may also focus fluorescence 708 from fluorescence material 702 to light detector 710. Lens 714 is shown in FIG. 7A as being located outside of elongated body 12. In some examples, elongated body 12 may have a thinner wall at a location for sensor 701 so lens 714 may be located closer to lumen 34 and amplify light 706 and fluorescence light 716. In another example, lens 714 may be a thin lens with curvature placed within or integral with lumen 34. In some example, lens 714 may be located between elongated body 12 and light source 704 and light detector 710, where light source 704 and light detector 710 are lower end devices requiring the amplification lens 714 provides to both amplify light 706 and fluorescence 716.

As described above, processing circuitry 200 may determine a temperature of fluid 504 within lumen 34 as part of the determination of the oxygen in fluid 504 (806). Fluorescence material 702 may be temperature-dependent and therefore to obtain a more accurate oxygen measurement the temperature of fluid 504 may be useful in calibrating the oxygen measurement. Processing circuitry 200 may use the temperature data collected from temperature sensor 502, temperature sensor 508, an estimated temperature based on a patient's body temperature, another sensor coupled to external device 24 or a temperature inputted by a user at user interface 204. Processing circuitry 200 may use the temperature to input into, e.g., an algorithm or a look up table to calibrate the oxygen calculation based on temperature of fluid 504 in combination with the rate of fluorescence decay detected by light detector 710.

Any suitable technique may be employed by processing circuitry 200 to determine the level of oxygen in fluid 504 based on the fluorescence detected by light detector 710. In some examples, processing circuitry 200 may reference a look up table in memory 202 to determine the oxygen level within fluid 504 based upon the detected fluorescence (e.g., alone or in combination with the determined temperature). In some examples, processing circuitry 200 may execute an algorithm on memory 202 which calculates the oxygen level based upon the fluorescence 708 detected or the fluorescence 708 and the determined temperature of fluid 504. In some examples, processing circuitry 200 may reference a lookup table stored in memory 719, memory 202 or memory 19. The lookup table may have a correlation for a specific fluorescence material 702 and what the fluorescence material's fluorescence time ($T_f$) is based upon a determined temperature of fluid 504. Based upon the temperature of fluid 504 and the fluorescence time ($T_f$) sensed by light detector 710 a lookup table may provide a corresponding oxygen level of fluid 504 based on the known variables. In another example, a lookup table may be implemented in algorithmic form where the variables are inputted into the algorithm by processing circuitry 200 and an oxygen level is presenting in display form on user interface 204 and/or through an audible form by a speaker on external device 24. In some examples, an alarm may be implemented through user interface 204 visually and/or audibly through a speaker if the oxygen level deviated outside of an upper or lower threshold. In another example, processing circuitry 200 may execute software 208 to perform the oxygen level determination based upon fluorescence time ($T_f$) and/or temperature calibration process of FIG. 8.

Figure 9A:
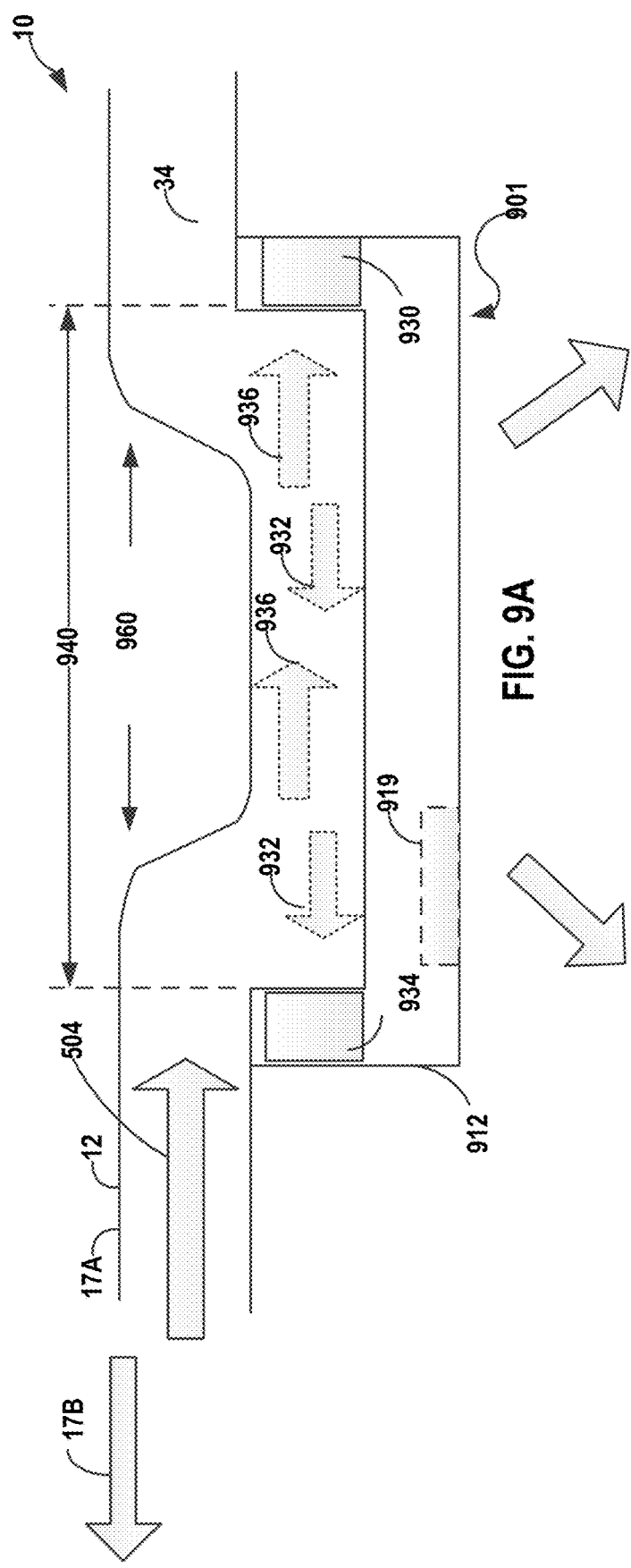
FIG. 9A is a diagram illustrating an example ultrasonic flow sensor used with a medical device according to the techniques of this disclosure.

FIG. 9A is a diagram illustrating an example ultrasonic flow sensor 901 used with medical device 10 according to the techniques of this disclosure. Ultrasonic flow sensor 901 may be an example of sensor 20 of medical device 10 (FIG. 1), may be used in place of sensor 20 or sensor 500, used in combination with sensor 20, sensor 500 or 701 or in addition to sensor 20, sensor 500 and sensor 701.

Ultrasonic sensor 901 may be configured to determine a flow rate of fluid 504 utilizing, e.g., a transit time technique or other technique described herein. Ultrasonic sensor 901 may include sensor body 912, first ultrasonic sensor 930, and second ultrasonic sensor 934. In some examples, sensor body 912 houses and/or couples first ultrasonic sensor 930 and second ultrasonic sensor 934 to each other, e.g., in a fixed position, on elongated body 12 of medical device 10. The term "ultrasonic" may refer to a signal (e.g., in the form of a sound wave) having a frequency above the approximate upper limit of human hearing, e.g., at or about 20 KiloHertz (KHz). Sensor 901 may determine a parameter based on the sensed transit times. Once the determination is made, processor 200 may control user interface 204 on external device 12 to present an indication of the determined value. For example, processor 200 may control user interface 204 of the external device to present an indication of a velocity and/or volumetric flow rate determine with flow sensor 901.

As will be describe further below, first and second ultrasonic sensors 930, 934 may each be configured to transmit signals (e.g., sound waves such as ultrasound waves) through fluid 504 as fluid 504 moves through lumen 34 of elongated body 12. For example, as shown in FIG. 9A, first ultrasonic sensor 930 may transmit first ultrasound waves 932 (or first signals 932) through fluid 504 and second ultrasonic sensor 934 may transmit second ultrasound waves 936 (or second signals 936) through fluid 504, e.g., in an opposite direction from that of the direction of first sound waves 932. First and second ultrasonic sensors 930 and 934 may receive the sound wave transmitted by the other of sensor 930 and 934, as well as transmit their respective sound waves. Put another way, first and second ultrasonic sensors 930 and 934 may each function as signal transmitters and signal receivers.

As shown in FIG. 9A, first and second ultrasonic sensors 930, 934 may be positioned such that first and second ultrasound waves 932 and 936, respectively, are transmitted substantially completely along the direction of flow of fluid 504 within lumen 34 (e.g., substantially parallel with the flow direction of fluid 504 and/or substantially parallel to the longitudinal axis of lumen 34). In other examples, first and second ultrasonic sensors 930, 934 may be positioned such that first and second ultrasound waves 932 and 936, respectively, are transmitted partially in the direction of the flow of fluid 504 (e.g., at a non-parallel angle to the direction of the flow of fluid 504 and/or the longitudinal axis of elongated body 12).

In some examples, first ultrasound sensor 930 may transmit first sound waves 932 in a path substantially parallel to the flow direction of fluid 504 in lumen 34 but in the opposite direction, and second first ultrasound sensor 934 may transmit second sound waves 936 in a path substantially parallel to the flow direction of fluid 504 in lumen 34 and in the same direction as the fluid flow. The first and second sound waves 932, 936 may be transmitted at substantially the same time or sequentially with each other. First sound waves 932 may be received by second ultrasound sensor 934 and the second sound waves 936 may be received by first ultrasound sensor 930. By comparing the transit time of second sound waves 936 with the flow of fluid 504 and the transit time of the first sound waves 932 against the flow of fluid 504, the average velocity of fluid 504 may be determined, e.g., by processor 200. From the average velocity, the flow rate of fluid 504 may be determined, e.g., by processor 200. In addition to, or as an alternative to, using transit time, ultrasonic sensor 901 may use frequency shifts to measure velocity and/or flow of fluid 504.

Figure 9B:
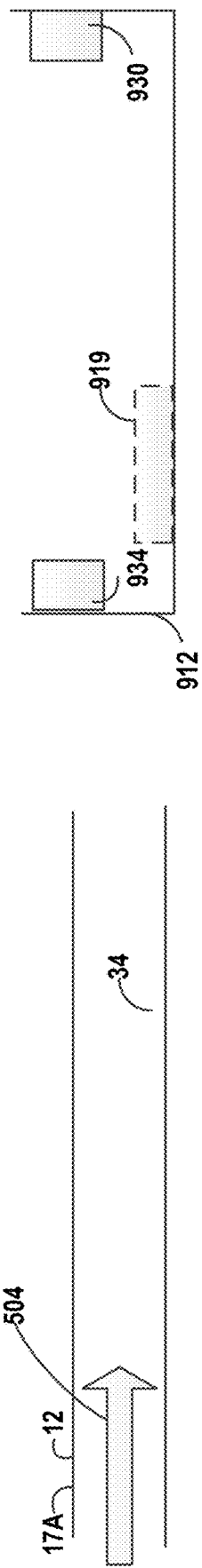
FIG. 9B is a diagram illustrating the example oxygen sensor of FIG. 9A separated into a disposable portion and a reusable portion according to techniques of this disclosure.

In some examples, ultrasonic sensors such as sensor 930 and 934, may be relatively expensive and, thus, cost prohibitive to use in a single-use medical device such as a single use catheter. In accordance with some examples of the disclosure, ultrasonic sensor 901 may be employed with medical device 10 (e.g., in the form of a Foley catheter system) such that sensor 901 or at least some components thereof are re-usable and not a non-separable part of a single-use catheter. Rather, as shown in FIG. 9B, sensor 901 may be detached from elongated body 12 and may be reused as to sense the flow of a fluid in another catheter while medical device 10 may be disposed after use with a single patient.

First 930 and second ultrasound sensors 934 may be any suitable receiver and/or transmitter configured to function in the manner described herein. In some examples, sensor 930 and 934 may include an ultrasonic transducer/transceiver such as linear, convex (standard or micro-convex), and phased array which are capable to transmitting and receiving ultrasonic sound waves. In some examples, first ultrasonic sensor 930 and second ultrasonic sensor 934 may be ultrasonic diffuse proximity sensors that employ a sonic transducer that allows for alternate transmission and reception of sound waves. The transducer may emit a series of ultrasonic pulses and then "listen" for an ultrasonic signal. Once the ultrasonic signal is received, ultrasonic sensor 930 and/or 934 signals an output to a control device such as a processing circuitry 200 or onboard processing circuitry (not shown in FIG. 9A or 9B). Ultrasonic sensors 930 and/or 934 may have their sensitivity, defined as the time window for "listen" cycles versus "send" cycles, adjusted via a teach-in button or a potentiometer. This output can easily be converted into useable distance information.

Ultrasonic sensors 930 and 934 may be power by any suitable power source, such as an onboard power source on ultrasonic flow sensor 901 or maybe powered by external device 24 providing power through connection 38 (FIG. 2).

In some examples, sensor body 912 may be comprised of most any material such as is common in printed circuit board design (e.g., FR-2 (phenolic cotton paper), FR-3 (cotton paper and epoxy), FR-4 (woven glass and epoxy), FR-5 (woven glass and epoxy), FR-6 (matte glass and polyester), G-10 (woven glass and epoxy), CEM-1 (cotton paper and epoxy), CEM-2 (cotton paper and epoxy)). In another example, sensor body 912 may have a flexible design so it may contour to the cylindrical shape of elongated body 12, thus ultrasonic sensors 930 and/or 934 as close to elongated body 12 as possible to ensure reliable ultrasonic sound transfer and sensor measurements. Flexible PCB materials include PI (polyimide) film and PET (polyester) film apart from which polymer film is also available like PEN (polyethylene nphthalate), PTFE and Aramid etc. Sensor body 912 may be removably coupled to elongated body such that sensor body 912 along with first and second sensor 930, 934 may be removed from elongated body 12 and be reused in another catheter for another procedure or application. In other examples, sensor body 912 may be left on elongated body and disposed of after use.

Sensor 901 may require calibration information to be accurate. Sensor 901 may require sensor-specific calibration information to produce an accurate measurement and compensate for variability in sensor 901. Sensor 901 may have memory 919 on sensor 901 that stores sensor calibration information that is used by external device 24 to more accurately read sensor data being sent from sensor 901. In another example, memory 19 may store sensor calibration information to calibrate sensor 901 based on the sensor calibration information stored by memory 19.

Ultrasonic flow sensor 901 may be a non-intrusive (e.g., clamp-on) transmission (e.g., a contra-propagating transit-time) flow meter. While the attachment mechanism for ultrasonic flow sensor 901 is not shown in FIG. 9A, elongated body 12 is shown with a bend 960 in elongated body 12 that generally corresponds to the "U" shape of sensor body 912. Bend 960 may be created by a clamping or coupling mechanism to attach sensor body 912 to elongated body 12 in the configuration shown in FIG. 9A. Once medical device 10 is ready for disposal, sensor body 912 may be uncoupled or detached from elongated body 12 for use with another catheter. In other examples, ultrasonic sensors 930 and/or 934 may be attached separately by a user to elongated body 12 without a sensor body 912 attaching sensor 930 and 934 to each other and elongated body 12. In other examples, ultrasonic sensors 930 and/or 934 may be integral with elongated body 12 and disposed of with elongated body 12 after the use of elongated body 12. However, ultrasonic sensors may be expensive and cost prohibitive to use in a single-use medical device. Ultrasonic flow sensor 901, therefore, may be reusable and coupled to sensor body 912 and not a permanent fixture on elongated body 12. Sensor body 912 may be releasably connected, e.g., mechanically with latches, snaps, threads, slides, cams, deformable sensor body, elastic connections, or magnetically.

Ultrasonic sensors 930 and 934 are shown facing one another in FIGS. 9A and 9B (e.g., such that first and second sound waves 932 and 936 are transmitted in a path that is substantially parallel to the flow direction of fluid 504 and/or the longitudinal axis of elongated body 12. However, ultrasonic sensors 930 and 934 may be positioned on elongated body 12 such that first and second sound waves 932 and 936 are transmitted in a path that that is at an angle to the flow direction of fluid 504 and/or the longitudinal axis of elongated body 12 Ultrasonic sensors 930 and 934 may also be tilted at an angle, from vertical, toward one another. In this manner, instead of facing each other where the ultrasonic signals travel directly between ultrasonic sensors 930 and 934, each of the ultrasonic pulses may be transmitted, through fluid 504 in lumen 34, bounce off of lumen 34 back through fluid 504 and be received by opposing ultrasonic sensors 930 and 934. Thus, the ultrasonic signals would take a "V" shaped or non-linear route between ultrasonic sensors 930 and 934. In other examples ultrasonic sensors 930 and 934 may be placed on elongated body 12 in most any fashion as long as ultrasonic sensor 930 may receive the ultrasonic transmission of ultrasonic sensor 934 and ultrasonic sensor 934 may receive the ultrasonic transmission of ultrasonic sensor 930 and a distance between ultrasonic sensors 930 and 934 may be known or determined (as will be discussed in detail below).

As described above, to determine a flow parameter of fluid 504 within lumen 34 (e.g., the average velocity and/or flow rate of fluid 504) first ultrasonic sensor 930 transmits a first ultrasonic signal 932 in a first direction through a fluid 504 flowing distally within lumen 34. Second ultrasonic sensor 934 may transmit a second ultrasonic signal 936 in a second direction through fluid 504 flowing distally within lumen 34. Second ultrasonic sensor 934 may be positioned on elongated body 12 proximal to first ultrasonic sensor 930. First ultrasonic sensor 930 may receive second ultrasonic signal 936 transmitted through fluid 504 flowing in lumen 34. Second ultrasonic sensor 934 may receive first ultrasonic signal 932 transmitted through fluid 504 flowing in lumen 34.

When first and second ultrasonic sensors 930 and 934 receive ultrasonic signals 936 and 932 respectfully, processing circuitry 200, may determine a first transit time of first ultrasonic signal 932 where the first transit time is a time from transmission from first ultrasonic sensor 930 to reception by second ultrasonic sensor 934. Processing circuitry 200 may determine a second transit time of second ultrasonic signal 936 where the second transit time is a time from transmission from second ultrasonic sensor 934 to reception by first ultrasonic sensor 930. Processing circuitry 200 may determine an average flow velocity of fluid 504 through lumen 34 based on the determined first and second transit times of first 932 and second ultrasonic signals 936. Processing circuitry 200 may also determine a flow rate of fluid 504 through lumen 34 based on the determined average flow velocity and a cross-sectional area of lumen 34.

Processing circuitry 200 may use the transit times of ultrasonic sounds 932 and 936, distance 940 and the inclination angle (which may be approximately zero degrees as first 930 and second ultrasonic sensor 934 are facing each other) with the following equation to find average velocity:

$$\text{Average velocity} = \frac{\text{Distance } 940}{2} * \frac{\text{Transit Time of } 932 - \text{Transit Time of } 936}{\text{Transit Time of } 932 * \text{Transit Time of } 936} \quad (1)$$

From the average velocity, processing circuitry may determine a volumetric flow rate. Flow rate may be calculated:

$$\text{Flow rate} = \text{Velocity} * \text{cross sectional area} \quad (2)$$

Processing circuitry 200 may determine other properties of fluid 504 utilizing known and determined attributes of fluid 504. For example, the acoustic properties of fluid 504 may affect ultrasonic flow sensing within lumen 34. Temperature, density, viscosity and suspended particulates in fluid 504 may impact ultrasonic flow sensing. Thus, memory 919, memory 19 or memory 202 may have the constitutions of many possible fluids stored on memory 919, memory 19 or memory 202. Processing circuitry 200 may then determine specific information regarding fluid 504 using flow rate, average flow velocity to calculate or look up density, specific gravity, temperature, and/or the like.

Ultrasonic sensors 930 and 934 are shown in FIGS. 9A and 9B facing one another and substantially parallel to the flow in lumen 34. Other examples may rely on the sound reflecting off portions of lumen 34 so ultrasonic sensors 930 and 934 do not necessarily have to be on opposite sides of lumen 34. In other examples, ultrasonic sensors 930 and 934 may be positioned at an angle to the direction of flow. In this example, equation (1) above could be modified to multiply the denominator by the cosign of the inclination angle from the direction of lumen 34. In another example, processing circuitry 200 may also detect frequency shifts through a doppler effect in first ultrasonic signal 932. Processing circuitry 200 may determine a change in average flow velocity based on the frequency shifts by dividing a doppler frequency by the frequency of first ultrasonic signal 932 and multiplying the speed of sound. Processing circuitry 200 may determine a change in flow rate of fluid 504 through lumen 34 based on the average flow velocity and cross-sectional area of lumen 34 over time.

Figure 10:
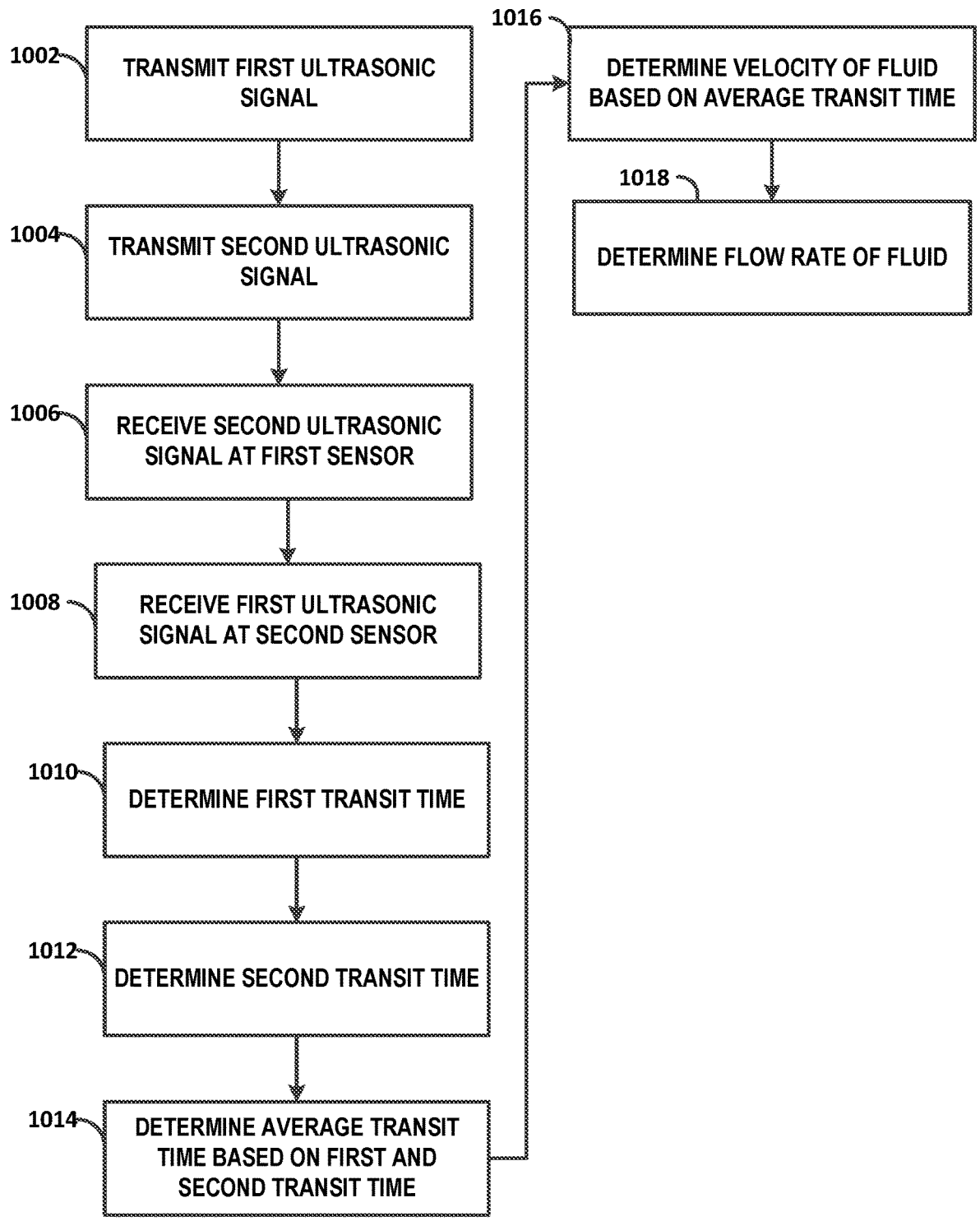
FIG. 10 is a flow diagram illustrating an example technique for monitoring or otherwise sensing flow rate of fluid within a lumen using the sensor of FIG. 9A according to techniques of this disclosure.

FIG. 10 is a flow diagram illustrating an example technique for monitoring or otherwise sensing flow rate of fluid within a lumen using sensor 901 of FIG. 9A according to techniques of this disclosure. For ease of description, the example technique of FIG. 10 is describe an being carried out under the control of processing circuitry 200. However, the example technique may be carried out any suitable processing circuitry either of medical device 10 or external device 24, for example.

Processing circuitry 200 may begin a flow rate determining process in response to a user instructing ultrasonic sensor 901 to begin sensing fluid flow, e.g., as inputted via external device 24. As stated above, ultrasonic sensor 901 may be powered by external device 24 routing power through connection 38 and/or by other suitable power source. A user may wait to initiate a flow rate sensing process until fluid 504 is flowing through lumen 34. Ultrasonic sensor 901 may provide a power source onboard sensor body 912 and be powered on separately by a power switch on sensor body 912 in another example. Once powered on, a user can begin a flow rate sensing process. Results may be displayed on user interface 204 including any alarms caused by resultant data being out of any threshold values. For example, if the transit times between ultrasonic sensors 930 and 934 were substantially the same, this may indicate there is little to no fluid flow, which may indicate a blockage of lumen 34.

Processing circuitry 200 may control first ultrasonic sensor 930 to transmit a first ultrasonic signal 932 in a first direction through fluid 504 flowing distally within lumen 34 defined by elongated body 12 (1002). Processing circuitry 200 may control second ultrasonic sensor 934 to transmit second ultrasonic signal 936 in a second direction through fluid 504 flowing distally within lumen 34 (1004). First ultrasonic signal 932 and second ultrasonic signal 936 may be transmitted simultaneously, substantially simultaneously or sequentially with each other.

As discussed above, first and second ultrasound sensor 930 and 934 may transmit sound waves 932 and 936 with ultrasonic frequencies. Ultrasound may refer to a sound wave with a frequency greater than the upper limit of human hearing, which is generally over 20 kHz. Among audible sounds not higher than 20 kHz, those not intended to be heard by humans may also be ultrasound. Ultrasound may travel through various media including gases, liquids and solids. Thus, ultrasonic signals 932 and 936 may travel efficiently through both elongated body 12 and fluid 504. However, as noted above, ultrasonic signals 932 and 936 will travel differently through both. Thus, processing circuitry may have a calibration factor for the time traveled in elongated body 12 if ultrasonic sensors 930 and 934 are located outside of elongated body 12.

Second ultrasonic sensor 934 may be positioned on elongated body 12 proximal to first ultrasonic sensor 930. First ultrasonic sensor 930 may receive second ultrasonic signal 936 transmitted through fluid 504 flowing in lumen 34 (1006). Second ultrasonic sensor 934 may receive first ultrasonic sound 932 transmitted through fluid 504 flowing in lumen 34 (1008).

Processing circuitry 200 may determine a first transit time of first ultrasonic signal 932 where the first transit time is a time from transmission from first ultrasonic sensor 930 to reception by second ultrasonic sensor 934 (1010). A second transit time of second ultrasonic signal 936 may be calculated by the processing circuitry 200, where the second transit time is a time from transmission from second ultrasonic sensor 934 to reception by first ultrasonic sensor 930 (1012).

An average transit time of ultrasonic signals 932 and 936 may be determined by processing circuitry 200, based on the determined first and second transit times of first 932 and the second ultrasonic signals 936 (1014).

A velocity of fluid 504 through lumen 34 may be determined by processing circuitry 200 based on the determined average transit time (1016). Processing circuitry 200 may determine a flow rate based on the flow velocity (1018).

In addition to, or as an alternative to, determining velocity and/or flow rate of fluid 504 based on the average transit time of first and second sound waves 932 and 936 through fluid 504, processing circuitry may determine the velocity and/or flow rate based on frequency shifts. For example, processing circuitry 200 may also detect frequency shifts through a doppler effect in first ultrasonic signal 932. Processing circuitry may determine a change in flow velocity based on the frequency shifts by dividing a doppler frequency by the frequency of first ultrasonic signal 932 and multiplying a speed of sound. Processing circuitry may determine a change in flow rate of fluid 504 through lumen 34 based on the flow velocity and a cross-sectional area of lumen 34 over time. Doppler shift may use the reflection of an ultrasonic signal off sonically reflective materials, such as solid particles or entrained air bubbles in flowing fluid 504, or the turbulence of fluid 504.

In another example, sensor 901 may be used to perform the above techniques on multiple different catheters by being removable from elongated body 12 and subsequently couple to another elongated body, e.g., in the manner described herein and shown in FIG. 9B.

While oxygen sensor 701 and ultrasonic flow sensor 901 are described above as being separate sensors, in some examples, sensor 20 on elongated body 12 in FIG. 1 may be a combination of each of oxygen sensor 701 and ultrasonic flow sensor 901. FIGS. 13A and 13B are diagrams illustration an example combination ultrasonic flow sensor and oxygen sensor for an elongated body according to techniques of this disclosure. Oxygen sensor 701 and ultrasonic flow sensor 901 may be combined on one sensor body 1312. Fluorescence material 702 may still be located within lumen 34. Sensor body 1312 may house first 930 and second ultrasonic sensor 934, light source 704 and light detector 710. Optional lens 714 may be coupled to disposable elongated body 12 or lens 714 may be part of reusable sensor body 1312. Sensor body 1312 may be coupled to elongated body 12 using any suitable coupling mechanisms or techniques. The coupling mechanism (not shown in FIG. 13A) used may create bend 960 that may allow for ultrasonic sensors 930 and 934 to substantially face one another. As described above with regard to sensors 701 and 901, in some examples, all or a portion of sensor body 1312 may be removably coupled from elongated body 12. FIG. 13B shows sensor body 1312 separated from elongated body 12, where elongated body include fluorescence material 702 and optional lens 714. In this manner, sensor body 1312 may be removed from elongated body 12, e.g., after elongated body 12 is no longer in use in a patient, so that sensor body 1312 may be coupled to another elongated body to provide the sensing functions described herein for sensors 701 and 901.

Figure 11:
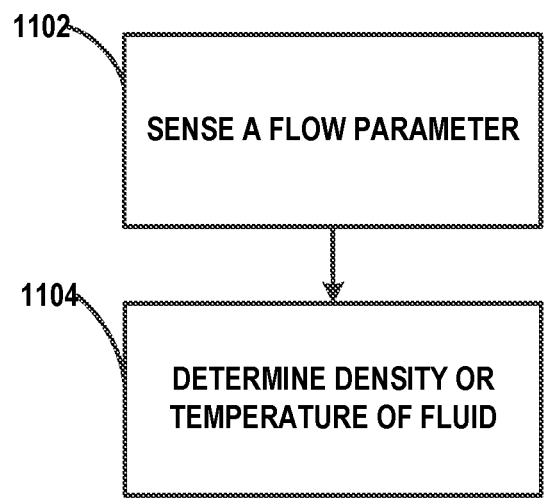
FIG. 11 is a flow diagram illustrating an example technique for determining density and/or temperature of a fluid within a lumen using a flow parameter according to techniques of this disclosure.

FIG. 11 is a flow diagram illustrating an example technique for determining a density and/or temperature of a fluid within a lumen of a catheter, such as drainage lumen 34 of medical device 10, in accordance with some examples of the disclosure. In some examples, sensor 20 of medical device 10 may be configured to sense a flow parameter of a fluid within lumen 34 of elongated body 12, and processing circuitry 200 and/or other processing circuitry may determine at least one of a density parameter or a temperature parameter of the fluid within lumen 34 based on the sensed flow parameter. For ease of description, the example of FIG. 11 is described primarily with regard to medical device 10 of FIG. 1 but it is understood that any catheter with a suitable sensor may be employed.

As shown in FIG. 11, sensor 20 located on elongated body 12 defining lumen 34 may sense a flow parameter of fluid 504 within lumen 34 of medical device 10 (1102). In one example, sensor 20 may be an ultrasonic sensor such as sensor 901. As described above, sensor 901 may be configured to determine the transit times of first and second sound waves 932 and 936 through fluid 504. Sensor 901 may measure the flow of fluid 504 through lumen 34 by measuring the difference in transit times of the sound waves traveling against the flow of fluid 504 and the transit time of the sound waves traveling with the flow of fluid 504. The difference in the transit times in conjunction with the channel dimensions and fluid characteristics can be used to calculate the flow rate of the fluid.

In addition to, or as an alternative to, using the transit time difference to calculate the flow rate, processor 200 may use the average transit time of the upstream and downstream direction, e.g., to calculate characteristics of fluid 504 such as temperature and/or density. For example, both temperature and density affect the speed of sound in a fluid. By measuring the average transit time in a known geometry (e.g., the geometry of lumen 34), the changes in density and temperature of fluid 504 may be calculated by processor 200.

As shown in FIG. 11, processing circuitry 200 may determine a density parameter (density/specific gravity value and/or change in density/specific gravity over a period of time) and/or temperature parameter (e.g., a temperature value or a change in temperature) of fluid 504 based on the sensed flow parameter (1104). For example, processing circuitry 200 may execute software 208, another algorithm stored on memory 919, memory 19 or memory 202 or reference a lookup table stored on memory 919, memory 19 or memory 202 to determine a density parameter or a temperature parameter of fluid 504 in lumen 34 based on the sensed flow parameter of fluid 504 (1104). Density and temperature both affect the speed of sound in fluid 504. If the distance between first 930 and second ultrasonic sensor 934 and time are known, the average velocity may be calculated. If the average velocity is known, temperature may be determined. A level of dissolved solids in fluid 504 may change the density and changes of density also change the speed of sound in fluid 504. If the average velocity and temperature are both known, the density may be calculated. There may be several lookup tables stored on memory 919, memory 19 or memory 202 where the lookup table may be based on the type of fluid within lumen 34.

In another example of the present disclosure, sensor 901 may be configured to sense at least one flow parameter of fluid 504 within lumen 34 of elongated body 12 to allow for medical device 10 or other device to determine (e.g., via processing circuitry 200) at least one of a density parameter or a temperature parameter of the fluid in lumen 34 based on the sensed flow parameter of the fluid. For example, sensor 901 where the flow is calculated by measuring the difference in the transit time of sound traveling against the fluid flow and the transit time of sound traveling with the fluid flow. The difference in the transit times in conjunction with dimensions of lumen 34 and the constitution of the fluid may be used to calculate the volumetric flow rate of the fluid. In addition, the average transit time of the upstream and downstream sound can be used to calculate characteristics of the fluid; such as temperature and density. By measuring the average transit time in a known geometry (e.g., lumen 34), changes in density and temperature may be calculated. For example, the temperature may be measured by a different means (e.g., a thermal dilution flow sensor 500) and this temperature in combination with the other known variables, such as lumen geometry and volumetric flow rate, may be used to calculate the density of the fluid by processing circuitry 200. In another example, processing circuitry 200 may determine the density of the urine using the average transit time when flow is high and the fluid is assumed to be at body temperature (e.g., 98.6° F.). In another example, body temperature may be measured using a temperature sensor at proximal end 12B, from other body temperature measuring devices, or assumed to be normal. The density of fluids, usually represented as the specific gravity, may be an important and common measurement (e.g. urinalysis). For example, the specific gravity of urine can be used to understand a patients' hydration status and the filtration capabilities of patient. The ability to measure urine density continuously and quickly can aid in understanding of the state of patient.

Further, processing circuitry 200, may not only make a determination of density at a specific time, but may also determine a density value for an average over a time period and/or measuring continuously or periodically to identify increases or decreases in density of a period of time even if density is not determined at a particular time period.

In another example, memory 919, memory 19 and/or memory 202 may have a lookup table providing a density and/or temperature for fluid 504 based upon detected average transit time changes and the constitution of fluid 504. The detected transit time changes may indicate a change in the speed of sound through fluid 504 indicating a possible change in density. Processing circuitry 200 may use an algorithm or a lookup table within memory 919, memory 19 or member 202 that correlates the change in transit time to a change in density and or a change in temperature.

Since temperature and density are inversely proportional, once a density is known a temperature may be determined, e.g., through an algorithm or a lookup table which correlates density to temperature for a specific fluid. If either of density or temperature are determined to be out of a threshold value, then an alarm may be sounded or given visually at user interface 204. During operation, density and temperature may be displayed on user interface 204 or external device 121 for a clinician to monitor In one example, the temperature of fluid 504 may be determined by processing circuitry 200 with known values (e.g., by one or more of the temperature sensors of sensor 500) and the temperature and ultrasound transit times may be used to calculate the density of fluid 504. In another example, the density of the fluid 504 may be measured using the average transit times determine by sensor 901, e.g., when flow is relatively high and fluid 504 is assumed to be at body temperature. In some examples, the body temperature of a patient may be measured using medical device 10 with a sensor at proximal end 12B, e.g., from other body temperature measuring devices, or assumed to be a normal temperature of urine or body temperature.

In an example of the present disclosure, the flow parameter sensed by sensor 20 may be an average transit time of fluid 504 through at least a portion of lumen 34, e.g., as describe above with regard to ultrasonic sensor 901. In another example, the flow parameter may be a temperature difference from thermal dilution sensor 500.

In some examples, the determined density parameter may be at least one of a density of fluid 504, a specific gravity of fluid 504, a change in the density of fluid 504 over time, or a change in the specific gravity of fluid 504. In some examples, the determined temperature parameter may be at least one of a temperature of fluid 504 or a change in the temperature of fluid 504 over time. Again, as described above, both temperature and density influence the speed of sound (e.g., sound waves) in a fluid. By measuring the average transit time, e.g. in the manner described herein with ultrasonic sensor 901, in a known geometry, the changes in density and temperature may be calculated.

The density of urine, usually represented as the specific gravity, is a measurement used in urinalysis. The specific gravity of urine may be used to understand a patients' hydration status and the filtration capabilities of a patient. The ability to measure urine density, e.g., substantially continuously and/or quickly, may aid in understanding of the state of patient. As such, using the technique of FIG. 11 to determine the density/specific gravity of fluid 504 within lumen 34, the system of FIG. 1 may aid a user in understanding the state of the patient, particularly with regard to hydration status and/or filtration capabilities of the patient in which medical device 10 is inserted as a urinary catheter.

Processing circuitry 200 may determine the density parameter or the temperature parameter of fluid 504 in lumen 34 based on the sensed flow parameter of fluid 504 and a geometry of lumen 34. Processing circuitry 200 may determine the geometry of lumen 34 in a variety of ways. In one example, the geometry of lumen 34 may be inputted by a user of external device 12 through user interface 204. The user may input a lumen diameter, or the user may input a measurement of medical device 10. For example, medical device 10 may be a 3 French catheter which has a 1 mm diameter (3Fr=1 mm). The geometry of lumen 34 may include a volume of at least a portion of lumen 34. For example, in some examples discussed above, a portion of lumen 34 may be widened or narrowed to control flow in a sensor monitoring location of elongated body 12. In this example, the user may input, at user interface 204, a special condition or special elongated body condition, such as a deviation in lumen size. The user may input a broader or narrower lumen size and the length of the size deviation. A volume change may be calculated for this deviation based on the know diameter (volume=length*n*diameter).

Figure 12:
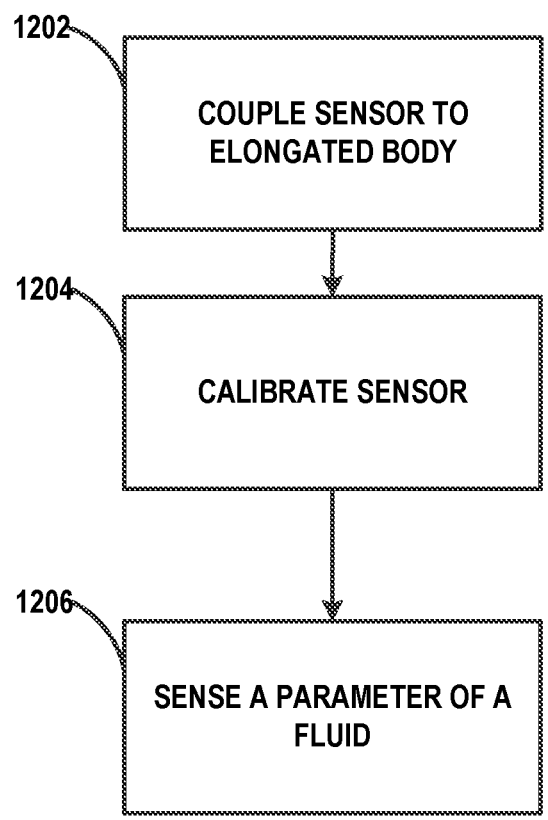
FIG. 12 is a flow diagram illustrating an example technique for calibrating sensors according to techniques of this disclosure.

In another example, processing circuitry 200 may determine a hydration status of a patient. Once processing circuitry 200 has determined a density, a specific gravity may be determined as well as specific gravity is the density of a substance divided by the density of water. If fluid 504 is too concentrated this may mean a patient's kidneys aren't functioning properly or they are dehydrated. This may initiate an alarm on user interface 204, either visual or auditory. If fluid 504 isn't concentrated enough it may mean a patient may have a rare condition called diabetes insipidus, which causes thirst and the excretion of large amounts of diluted urine. Knowing urine specific gravity is a quick way a clinician to tell if the patient's kidneys are trying to compensate for some abnormality. Specific gravity may be helpful in indicating any of dehydration or overhydration, heart failure, shock, diabetes, insipidus, kidney failure, kidney infection, urinary tract infection, hyponatremia, or low sodium levels, hypernatremia, or elevated sodium levels FIG. 12 is a flow diagram illustrating an example technique for calibrating one or more sensors of a catheter, such as, medical device 10, according to techniques of this disclosure. The technique of FIG. 12 may be employed to calibrate one or more sensors employed by a catheter such as sensors 20, 500, 701, and/or 901. In some examples, the technique of FIG. 12 may be used in cases in which medical device 10 includes both an elongated body 12 that is configured to be disposed after use, while sensors 20, 500, 701, and/or 901 may be detachably coupled to elongated body 12 so that sensor 20, 500, 701, and/or 901 may be reused and/or may allow for one or more of a variety of different sensors to be coupled to elongated body 12 after manufacture of elongated body 12. As described below, elongated body 12 may include a memory 19 that stores calibration information that is specific to elongated body 12. Each sensor 20, 500, 701, and/or 901 that may be coupled to elongated body 12, may have a memory 519, 719 and 919 that stores calibration information specific to sensor 500, 701, and/or 901 respectively for calibration used for the sensing functionality. While examples are described with regard to sensor 20, 500, 701, and/or 901, such a technique may be employed for any sensor that is coupled to elongated body 12 of medical device 10.

As shown in FIG. 12, one or more of sensors 20, 500, 701 or 901 may be releasably coupled to elongated body 12 (1202). The coupling may occur in most any manner such as temporary adhesives, clamping, clipping, pad mounting, magnetic mounting etc. One or more of each sensor may have a memory 519, 719 and/or 919.

Memories 519, 719, and/or 9191 may store sensor calibration information that is useful to one or more of sensors 20, 500, 701 or 901. Sensors 20, 500, 701 or 901 may be calibrated based on the sensor calibration information stored by memories 519, 719, and/or 919 (1204). One of sensors 20, 500, 701 or 901 may be configured to sense one or more parameters of a fluid 504 within lumen 34 of elongated body 12 and adjust the sensed one or more parameters based on the stored calibration information (1206).

Calibration information may be required for a new instrument. For example, if sensor 20, 500, 701, or 901 are swapped out with a different sensor or replaced with a similar sensor, processing circuitry 200 may need obtain calibration information from the new sensor. This calibration information may be stored on a memory on the new sensor that may also be necessary for replacement pieces or parts of sensor 20, 500, 701, or 901. For example, replacement of a temperature sensor 502 on sensor 500. Calibration may also be necessary after an instrument has been repaired or modified.

Each of sensor 20, 500, 701, or 901 may need calibration after a specified time period has elapsed. For example, after sensor 20 has been used for 100 hours it may be necessary to calibrate sensor 20 to ensure sensor 20 is still operating properly. In some instances, an operator may desire each sensor to be calibrated before each procedure to ensure proper readings during procedures. Processing circuitry 200 may monitor readings provided by sensors 20, 500, 701 and 901 and whenever observations appear questionable or instrument indications do not match the output of surrogate instruments a calibration may be performed.

A sensor such as sensor 20, 500, 701, and/or 901 may require calibration information to be accurate. As described above, a flow sensor 500 and/or 901 and an oxygen sensor 701 may be incorporated into medical device 10 and, in some examples, may be removably coupled to elongated body 12. One or more of these sensors may require sensor-specific calibration information to produce relatively accurate measurement to compensate for variability in the sensors. For example, thermal dilution flow sensor 500 may require information that correlates actual flow to a measured temperature difference. Variability in the temperature differences occurs due to small differences in heater member 512, temperature sensors 502 and/or 508, the lumen dimensions, or the position of the heater member 512 or temperature sensors 502 and/or 508. Calibration information on memory 519 could provide known calibration standards for each of heater member 512, temperature sensors 502 and 508, dimensions of a known elongated body 12. This information can be used to correct for manufacturing variations in temperature sensors 502 and 508, heater member 512, lumen 34, and other geometries, as well as used in algorithms or lookup tables to provide information such as geometry of lumen 34 or flow calculations dependent on the location of temperature sensor 508 and its distance from heating member 512. In an example, the calibration information may provide coefficients for an algorithm that fit flow data to temperature changes for a specific sensor for a specific type of fluid.

By including the sensor calibration in or on the sensor, the accuracy of the measurements as well as the flexibility to change the components in the sensor or offer different ranges of sensors in the future, is possible without changing the software in the monitoring.

The sensor calibration information may be specific calibration information for manufacturing variations within sensor 20, 500, 701 or 901.

In one example where the calibration information may be specific to sensor 500, the calibration information may include, manufacturing variations in sensor 500, dimensions of lumen 34 (e.g., for area, volume, density and temperature calculations), a position of heating member 512 on elongated body 12, a position of first temperature sensor 502 on elongated body 12, a position of second temperature sensor 508 on elongated body 12, a type of heating member 512, a type of first temperature sensor 502, a type of second temperature sensor 508 or a constitution of the fluid 504 within lumen 34.

The calibration information on memory 519 may be used in the process of adjusting the output or indication on sensors 502 and/or 508 to agree with value of the applied standard, within a specified accuracy. For example, thermometer 502 or 508 may be calibrated so the error of indication or the correction is determined and adjusted (e.g. via calibration constants) so that it shows the true temperature at specific points. This is the display at user interface 204.

In another example, where the calibration information may be specific to ultrasonic flow sensor 901 and may include, manufacturing variations in sensor 901 (e.g., small variations in the frequency of first 930 and/or second ultrasonic sensor 934 and any geometric variability to the sensor assembly), dimensions of lumen 34 (e.g., for area, volume, density and temperature calculations), a position of first ultrasonic sensor 930 on elongated body 12, a position of second ultrasonic sensor 934 on elongated body 12 (e.g., distance 940 between first 930 and second ultrasonic sensor 934), a type of first ultrasonic sensor 630, a type of second ultrasonic sensor 634 or a constitution of the fluid 504 in lumen 34 (e.g., urine, blood, etc.).

The calibration information located on memory 919 may be used by processing circuitry 200 that, under specified conditions, establishes a relation between the quantity values measured by sensors 20, 500, 701, or 901 with measurement uncertainties provided by measurement standards stored on memory 919. Processing circuitry 200 may use this information to establish a relation for obtaining a measurement result. Processing circuitry 200 may perform a calibration process or a comparison to reduce or eliminate measurement uncertainty in relating the accuracies of sensors 20, 500, 701, and 901.

In another example, where the calibration information may be specific to oxygen sensor 701, the calibration information may include: dimensions of lumen 34, fluorescing properties of fluoresce material 702 (e.g., different fluoresce materials may react differently to different fluids), a type of light source 704 (e.g., one light source may be brighter than another or emit a different wavelength of light) or a type of light receptor 610. For example, light source 704 may have variations in intensity, wavelength (e.g., a manufacturing variation), etc. There may also exist minor assembly variations in materials and alignments that may affect the accuracy of the measurements. As discussed above, processing circuitry 200 may compare a known fluorescence rate with a detected fluorescence rate of fluoresce material 702. If the detected fluorescence is off by a certain amount, processing circuitry 200 may apply a calibration factor to account for the offset. This process may be extended to light 706 emitted by light source 704. For example, if light 706 is replaced, processing circuitry may use calibration information stored on memory 719 to account for any difference and then take this difference into account with measurements coming from light detector 710.

Many sensors provide more accurate readings when calibrated or provided with calibration information to ensure accurate readings. Sensors 20, 500, 701 and 901 may use sensor-specific calibration information to compensate for variability in sensors 20, 500, 701 and 901 and produce a more accurate measurement.

For example, flow sensor 500 may use information that correlates actual flow to measured temperature difference. Variability in the temperature differences occur due to small differences in heater member 512, temperature sensors 502 and 508, the lumen dimensions, or the position of heater element 512 or temperature sensors 502 and 508.

Similarly, oxygen sensor 701 may have specific calibration parameters related to fluorescing material 702 used, as well as the specifics of light source 704 and light detector 710.

Sensor calibration data onboard memories 519, 719 or 919 may calibrate measurements as well as allow the flexibility to change the components in sensors 20, 500, 701 and 901 or offer different ranges of sensors 20, 500, 701 and 901 in the future without changing software 208.

Various examples have been described. These and other examples are within the scope of the following claims. For purposes of this disclosure, the operations shown FIGS. 6, 8, 10, 11 and 12 do not need to be executed in the manner suggested by the illustrations and, unless specifically stated so, may be executed in any order. Further, the term substantially is to be given its standard definition of to a great or significant extent or for the most part; essentially.

The following is a non-limiting list of examples that are in accordance with one or more techniques of this disclosure.

Example 1A. A device comprising: an elongated body defining a lumen, the elongated body comprising a proximal portion and a distal portion; an anchoring member positioned on the proximal portion of the elongated body; a first temperature sensor configured to sense a first temperature of a fluid at a first location in the lumen; a second temperature sensor configured to sense a second temperature of the fluid at a second location in the lumen, the first location being proximal to the second location; and a heating member located proximal to the second temperature sensor, the heating member configured to heat the fluid within the lumen.

Example 2A. The device of example 1A, further comprising processing circuitry configured to determine a flow of the fluid within the lumen based on a difference between the first temperature and the second temperature.

Example 3A. The device of any one of examples 1A-2A, wherein the heating member is located between the first temperature sensor and the second temperature sensor.

Example 4A. The device of any one of examples 1A-2A, wherein the heating member is located proximal to the first temperature sensor and the second temperature sensor.

Example 5A. The device of any one of examples 1A-4A, wherein the first temperature sensor, the second temperature sensor, and the heating member are configured to be releasably coupled to the elongated body.

Example 6A. The device of any of examples 1A-5A, wherein a diameter of the lumen is a smaller diameter to decrease a flow of the fluid.

Example 7A. The device of any of examples 1A-6A, wherein the first temperature sensor and the second temperature sensors each comprise at least one of a thermocouple sensor or a thermistor sensor.

Example 8A. The device of any of examples 1A-7A, further comprising an oxygen sensor configured to sense oxygen concentration in the fluid within the lumen, wherein the oxygen sensor is configured to be calibrated based on at least one of the first sensed temperature or the second sensed temperature.

Example 9A. The device of example 8A, wherein the oxygen sensor comprises:

a fluoresce material, located within the lumen, configured to contact and react with the fluid in the lumen; a light source configured to emit a specific wavelength of light, the fluoresce material within the fluid being fluorescent when exposed to the wavelength of light and oxygen in the fluid, where the greater the amount of oxygen in the fluid the lower an intensity in fluoresce in the fluid; and a light detector configured to detect the emitted fluorescence.

Example 10A. The device of example 9A, wherein the amount of fluorescence given off by the fluoresce material is temperature dependent.

Example 11A. The device of any of examples 8A-10A, wherein the oxygen sensor is located proximal to the heating member, and the oxygen sensor is calibrated based on the first sensed temperature.

Example 12A. The device of any of examples 1A-11A, wherein the elongated body comprises a Foley catheter.

Example 1B. A method comprising: heating, with a heating member a fluid within a lumen defined by an elongated body comprising a proximal portion and a distal portion; sensing, with a first temperature sensor, a first temperature of a fluid at a first location in the lumen; and sensing, with a second temperature sensor, a second temperature of the fluid at a second location in the lumen, the first location being proximal to the second location.

Example 2B. The method of example 1B, further comprising determining, with processing circuitry, a flow of the fluid within the lumen based on a difference between the first temperature and the second temperature.

Example 3B. The method of any of examples 1B-2B, wherein the heating member is located between the first temperature sensor and the second temperature sensor.

Example 4B. The method of any of examples 1B-2B, wherein the heating member is located proximal to the first temperature sensor and the second temperature sensor.

Example 5B. The method of any of examples 1B-4B, further comprising releasably coupling the first temperature sensor, the second temperature sensor, and the heating member to the elongated body.

Example 6B. The method of any of examples 1B-5B, wherein a diameter of the lumen is a smaller diameter to decrease a flow of the fluid.

Example 7B. The method of any of examples 1B-6B, wherein the first temperature sensor and the second temperature sensors each comprise at least one of a thermocouple sensor or a thermistor sensor.

Example 8B. The method of any of examples 1B-7B, further comprising: sensing, with an oxygen sensor, oxygen concentration in the fluid within the lumen; and calibrating the oxygen sensor based on at least one of the first sensed temperature or the second sensed temperature.

Example 9B. The method of example 8B, further comprising: controlling a light source to emit light to expose a fluorescence material to the emitted light, wherein the fluorescence material within a fluid is configured to fluoresce when exposed to the light in the lumen defined by an elongated body comprising a proximal portion and a distal portion; detecting, with a light detector, the fluorescence of the fluorescence material; and detecting, based on the detected fluorescence, oxygen in the fluid within the lumen.

Example 10B. The method of example 9B, wherein the amount of fluorescence given off by the fluoresce material is temperature dependent.

Example 11B. The method of any of examples 8B-10B, wherein the oxygen sensor is located proximal to the heating member, and the oxygen sensor is calibrated based on the first sensed temperature.

Example 12B. The method of any of examples 8B-11B, wherein the oxygen sensor is located distal to the device, and the oxygen sensor is calibrated based on the second sensed temperature.

Example 1C. A device comprising: an elongated body defining a lumen, the elongated body comprising a proximal portion and a distal portion; an anchoring member positioned on the proximal portion of the elongated body; a first temperature sensor configured to sense a first temperature of a fluid at a first location in the lumen; a second temperature sensor configured to sense a second temperature of the fluid at a second location in the lumen, the first location being proximal to the second location; a heating member located proximal to the second temperature sensor, the heating member configured to heat the fluid within the lumen; processing circuitry configured to determine a flow of the fluid within the lumen based on a difference between the first temperature and the second temperature; and an oxygen sensor configured to sense oxygen concentration in the fluid within the lumen, wherein the oxygen sensor is configured to be calibrated based on at least one of the first sensed temperature or the second sensed temperature.

Example 1D. A medical device system comprising: an elongated body defining a lumen, the elongated body comprising a proximal portion and a distal portion; a sensor coupled to the elongated body, the sensor comprising: a first ultrasonic sensor configured to transmit a first ultrasonic signal in a first direction through a fluid flowing distally within the lumen; and a second ultrasonic sensor configured to transmit a second ultrasonic signal in a second direction through the fluid flowing distally within the lumen, the second ultrasonic sensor being positioned on the elongated body proximal to the first ultrasonic sensor; wherein the first ultrasonic sensor is configured to receive the second ultrasonic signal transmitted through the fluid flowing in the lumen; wherein the second ultrasonic sensor is configured to receive the first ultrasonic sound transmitted through the fluid flowing in the lumen.

Example 2D. The system of example 1D, further comprising processing circuitry configured to: determine a first transit time of the first ultrasonic signal, the first transit time is a time from transmission from the first ultrasonic sensor to reception by the second ultrasonic sensor; and determine a second transit time of the second ultrasonic signal, the second transit time is a time from transmission from the second ultrasonic sensor to reception by the first ultrasonic sensor; and determine a flow velocity of the fluid through the lumen based on the determined first and second transit times of the first and the second ultrasonic signals.

Example 3D. The system of example 2D, wherein the processing circuitry is configured to determine a flow rate of the fluid through the lumen based on the determined flow velocity and a cross-sectional area of the lumen.

Example 4D. The system of example 2D, wherein the processing circuitry is configured to determine an average velocity by dividing a distance between the first and the second ultrasonic sensors with the first and second transit times and.

Example 5D. The system of example 4D, wherein the average velocity is determined by multiplying half the distance between the first and second sensors by the difference of the transit time of the first ultrasonic signal and the second ultrasonic signal divided by the multiplication of the transit time of the first ultrasonic signal and the second ultrasonic signal.

Example 6D. The system of examples 2D, wherein the processing circuitry is configured to detect frequency shifts through a doppler effect in the first ultrasonic signal.

Example 7D. The system of example 6D, wherein the processing circuitry is configured to determine a change in flow velocity based on the frequency shifts by dividing a doppler frequency by the frequency of the first ultrasonic signal and multiplying a speed of sound.

Example 8D. The system of any of examples 6D-7D, wherein the processing circuitry is configured to determine a change in flow rate of the fluid through the lumen based on the flow velocity and a cross-sectional area of the lumen over time.

Example 9D. The system of any of examples 1D-8D, wherein the sensor coupled to the elongated body is configured to be removed from the elongated body.

Example 10D. The system of any of examples 1D-9D, wherein the sensor is configured to be reused.

Example 11D. The system of any of examples 1D-10D, wherein the sensor further comprises an oxygen sensor.

Example 12D. The system of example 11D, wherein the oxygen sensor comprises: a fluoresce material, located within the lumen, configured to contact and react with the fluid in the lumen; a light source configured to emit a specific wavelength of light, the fluoresce material within the fluid being fluorescent when exposed to the wavelength of light and oxygen in the fluid, where the greater the amount of oxygen in the fluid the lower an intensity in fluoresce in the fluid; and a light detector configured to detect the emitted fluorescence.

Example 13D. The system of any of examples 1D-12D, wherein the first ultrasonic sensor at least partially faces the second ultrasonic sensor.

Example 14D. The system of any of examples 1D-13D, wherein the first ultrasonic sensor transmits the first ultrasonic signal, at least partially, with a flow direction of the fluid and the second ultrasonic sensor transmits the second ultrasonic signal, at least partially, against the flow direction of the fluid.

Example 15D. The system of examples 1D-13D, wherein the first ultrasonic sensor or the second ultrasonic sensor is substantially parallel to the fluid flow in the lumen.

Example 16D. The system of any of examples 1D-12D, wherein the first ultrasonic sensor and the second ultrasonic sensor are pointed at an angle to the fluid flow and the first and the second ultrasonic signal are reflected off of a lumen wall before they are received.

Example 17D. The system of any of examples 1D-16D, wherein the elongated body comprises a Foley catheter.

Example 1E. A method comprising: transmitting, with a first ultrasonic sensor, a first ultrasonic signal in a first direction through a fluid flowing distally within a lumen defined by an elongated body comprising a proximal portion and a distal portion; transmitting, with a second ultrasonic sensor being positioned on the elongated body proximal to the first ultrasonic sensor, a second ultrasonic signal in a second direction through the fluid flowing distally within the lumen; receiving, with the first ultrasonic sensor, the second ultrasonic signal transmitted through the fluid flowing in the lumen; and receiving, with the second ultrasonic sensor, the first ultrasonic sound transmitted through the fluid flowing in the lumen.

Example 2E. The method of example 1E, further comprising: determining, with processing circuitry, a first transit time of the first ultrasonic signal, wherein the first transit time is a time from transmission from the first ultrasonic sensor to reception by the second ultrasonic sensor; and determining, with the processing circuitry, a second transit time of the second ultrasonic signal, wherein the second transit time is a time from transmission from the second ultrasonic sensor to reception by the first ultrasonic sensor; and determining, with the processing circuitry, a flow velocity of the fluid through the lumen based on the determined first and second transit times of the first and the second ultrasonic signals.

Example 3E. The method of example 2E, further comprising determining, with the processing circuitry, a flow rate of the fluid through the lumen based on the determined flow velocity and a cross-sectional area of the lumen.

Example 4E. The method of example 2E, further comprising determining, with the processing circuitry, an average velocity by dividing a distance between the first and the second ultrasonic sensors with the first and second transit times.

Example 5E. The method of example 4E, wherein the average velocity is determined by half the distance between the first and second sensors, multiplied by, the difference of the transit time of the first ultrasonic signal and the second ultrasonic signal, divided by, the transit time of the first ultrasonic signal multiplied by the transit time of the second ultrasonic signal.

Example 6E. The method of example 2E, further comprising detecting, with the processing circuitry, frequency shifts through a doppler effect in the first or the second ultrasonic signal.

Example 7E. The method of example 6E, further comprising determining, with the processing circuitry, a change in flow velocity based on the frequency shifts by dividing a doppler frequency by the frequency of the first ultrasonic signal and multiplying a speed of sound.

Example 8E. The method of any of examples 2E-3E, further comprising determining, with the processing circuitry, a change in flow rate of the fluid through the lumen based on the flow velocity and a cross-sectional area of the lumen over time.

Example 9E. The method of any of examples 1E-8E, wherein the first ultrasonic sensor and the second ultrasonic sensor are coupled to a sensor body configured to be removably attached to the elongated body.

Example 10E. The method of any of examples 1E-9E, wherein the sensor body is configured to be reusable.

Example 11E. The method of any of examples 1E-10E, wherein the sensor body further comprises an oxygen sensor.

Example 12E. The method of example 11E, further comprising: controlling a light source to emit light to expose a fluorescence material to the emitted light, wherein the fluorescence material within a fluid is configured to fluoresce when exposed to the light in the lumen defined by an elongated body comprising a proximal portion and a distal portion; detecting, with a light detector, the fluorescence of the fluorescence material; and detecting, based on the detected fluorescence, oxygen in the fluid within the lumen.

Example 13E. The method of any of examples 1E-12E, wherein the first ultrasonic sensor at least partially faces the second ultrasonic sensor.

Example 14E. The method of example 13E, wherein the first ultrasonic sensor transmits the first ultrasonic signal, at least partially, with a flow direction of the fluid and the second ultrasonic sensor transmits the second ultrasonic signal, at least partially, against the flow direction of the fluid.

Example 15E. The method of example 13E, wherein the first ultrasonic sensor or the second ultrasonic sensor is substantially parallel to the fluid flow in the lumen.

Example 16E. The method of 1E, wherein the first ultrasonic sensor and the second ultrasonic sensor are pointed at an angle to the fluid flow and the first and the second ultrasonic signal are reflected off of a lumen wall before they are received.

Example 17E. The method of any of examples 1E, 13E, 14E and 16E, wherein the first ultrasonic sensor is located on an opposite side of the elongated body from the second ultrasonic sensor.

Example 1F. A medical device system comprising: an elongated body defining a lumen, the elongated body comprising a proximal portion and a distal portion; a sensor coupled to the elongated body, the sensor comprising: a first ultrasonic sensor configured to transmit a first ultrasonic signal in a first direction through a fluid flowing distally within the lumen; a second ultrasonic sensor configured to transmit a second ultrasonic signal in a second direction through the fluid flowing distally within the lumen, the second ultrasonic sensor being positioned on the elongated body proximal to the first ultrasonic sensor; and processing circuitry configured to: determine a first transit time of the first ultrasonic signal, the first transit time is a time from transmission from the first ultrasonic sensor to reception by the second ultrasonic sensor; determine a second transit time of the second ultrasonic signal, the second transit time is a time from transmission from the second ultrasonic sensor to reception by the first ultrasonic sensor; and determine a flow velocity of the fluid through the lumen based on the determined first and second transit times of the first and the second ultrasonic signals. wherein the first ultrasonic sensor is configured to receive the second ultrasonic signal transmitted through the fluid flowing in the lumen; wherein the second ultrasonic sensor is configured to receive the first ultrasonic sound transmitted through the fluid flowing in the lumen.

Example 1G. A system comprising: an elongated body defining a lumen, the elongated body comprising a proximal portion and a distal portion; an anchoring member positioned on the proximal portion of the elongated body; a fluorescence material configured to be located within the lumen with a fluid in the lumen; a light source configured to emit light to expose the fluorescence material to the emitted light, wherein the fluorescence material within the fluid is configured to fluoresce when exposed to the light in the lumen; and a light detector configured to detect the fluorescence of the fluorescence material, wherein the device is configured to detect oxygen in the fluid within the lumen based on the detected fluorescence.

Example 2G. The system of example 1G, wherein the light source and the light detector are both releasably coupled to the elongated body.

Example 3G. The system of any of examples 1G-2G, further comprising a sensor body configured to be releasably coupled to the elongated body, the sensor body supporting the light source and the light detector.

Example 4G. The system of any of examples 1G-3G, further comprising a lens configured to be placed on the elongated body in between the fluorescence material and light source.

Example 5G. The system of example 4G, wherein the lens is configured to focus the light to the fluorescence material in the lumen.

Example 6G. The system of any of examples 4G-5G, wherein the lens is configured to focus the fluorescence from the fluorescence material to the light detector.

Example 7G. The system of any of examples 1G-3G, further comprising a lens configured to be placed on the elongated body in between the fluorescence material and the light source.

Example 8G. The system of example 7G, wherein the lens is configured to be coupled to the reusable base portion.

Example 9G. The system of any of examples 3G-8G, further comprising: a first ultrasonic sensor configured to transmit a first ultrasonic signal in a first direction through a fluid flowing distally within the lumen; and a second ultrasonic sensor configured to transmit a second ultrasonic signal in a second direction through the fluid flowing distally within the lumen, the second ultrasonic sensor being positioned on the elongated body proximal to the first ultrasonic sensor.

Example 10G. The system of example 9G, wherein the first and the second ultrasonic sensor are coupled to the reusable base portion.

Example 1H. A method comprising: controlling a light source to emit light to expose a fluorescence material to the emitted light, wherein the fluorescence material within a fluid is configured to fluoresce when exposed to the light in the lumen defined by an elongated body comprising a proximal portion and a distal portion; detecting, with a light detector, the fluorescence of the fluorescence material; and determining, based on the detected fluorescence, oxygen in the fluid within the lumen.

Example 2H. The method of example 1H, wherein the light source and the light detector are both releasably coupled to the elongated body.

Example 3H. The method of any of examples 1H-2H, wherein the light source and the light detector are coupled to a sensor body configured to be releasably coupled to the elongated body.

Example 4H. The method of any of examples 1H-3H, further comprising focusing the emitted light through a lens configured to be placed on the elongated body in between the fluorescence material and light source.

Example 5H. The method of example 4H, wherein the lens is configured to focus the light to the fluorescence material in the lumen.

Example 6H. The method of and of examples 4H-5H, further comprising focusing the fluorescence from the fluorescence material to the light detector.

Example 7H. The method of any of examples 4H-6H, wherein the lens is located on the elongated body in between the fluorescence material and the light source.

Example 8H. The method of example 7H, wherein the lens is configured to be coupled to the reusable base portion.

Example 9H. The method of any of examples 3H-8H, further comprising: transmitting, with a first ultrasonic sensor, a first ultrasonic signal in a first direction through a fluid flowing distally within the lumen; and transmitting, with a second ultrasonic sensor, a second ultrasonic signal in a second direction through the fluid flowing distally within the lumen, the second ultrasonic sensor being positioned on the elongated body proximal to the first ultrasonic sensor.

Example 10H. The method of any of examples 1H-9H, wherein the elongated body comprises a Foley catheter.

Example 1I. A system comprising: an elongated body defining a lumen, the elongated body comprising a proximal portion and a distal portion; an anchoring member positioned on the proximal portion of the elongated body; a fluorescence material configured to be located within the lumen with a fluid in the lumen; a light source configured to emit light to expose the fluorescence material to the emitted light, wherein the fluorescence material within the fluid is configured to fluoresce when exposed to the light in the lumen; a light detector configured to detect the fluorescence of the fluorescence material; a sensor body configured to be releasably coupled to the elongated body, the sensor body supporting the light source and the light detector; a lens configured to be placed on the elongated body in between the fluorescence material and light source; a first ultrasonic sensor configured to transmit a first ultrasonic signal in a first direction through a fluid flowing distally within the lumen; and a second ultrasonic sensor configured to transmit a second ultrasonic signal in a second direction through the fluid flowing distally within the lumen, the second ultrasonic sensor being positioned on the elongated body proximal to the first ultrasonic sensor; wherein the device is configured to detect oxygen in the fluid within the lumen based on the detected fluorescence.

Example 1J. A system comprising: an elongated body defining a lumen, the elongated body comprising a proximal portion and a distal portion; an anchoring member positioned on the proximal portion of the elongated body; a sensor located on the elongated body, the sensor configured to sense at least one flow parameter of a fluid within the lumen; and processing circuitry configured to determine at least one of a density parameter or a temperature parameter of the fluid in the lumen based on the sensed at least one flow parameter of the fluid.

Example 2J. The system of example 1J, wherein the at least one flow parameter sensed by the sensor comprises an average transit time of the fluid through at least a portion of the lumen.

Example 3J. The system of any of examples 1J-2J, wherein the density parameter comprises at least one of a density of the fluid, a specific gravity of the fluid, a change in the density of the fluid, or a change in the specific gravity of the fluid.

Example 4J. The system of any of examples 1J-3J, wherein the temperature parameter comprises at least one of a temperature of the fluid or a change in the temperature of the fluid.

Example 5J. The system of any of examples 1J-4J, wherein the processing circuitry is configured to determine the at least one of the density parameter or the temperature parameter of the fluid in the lumen based on the sensed at least one flow parameter of the fluid and a geometry of the lumen.

Example 6J. The system of example 5J, wherein the geometry of the lumen includes a volume of at least a portion of the lumen.

Example 7J. The system of any of examples 1J-7J, further comprising a temperature sensor configured to determine a temperature of the fluid within the lumen, wherein the processing circuitry is configured to determine the density parameter of the fluid based on the at least one flow parameter and the determined temperature of the fluid.

Example 8J. The system of example 7J, wherein the temperature sensor is located on the elongated body.

Example 9J. The system of example 1J, wherein the processing circuitry is configured to determine the density parameter of the fluid based on the at least one flow parameter and an estimated temperature of the fluid.

Example 10J. The system of example 9J, wherein the estimated temperature of the fluid is estimated based on a sensed body temperature of a patient in which the elongated body is at least partially inserted.

Example 11J. The device of any of examples 1J-10J, wherein the processing circuitry is configured to: determine the density parameter of the patient based on the sensed at least one flow parameter of the fluid, and determine a hydration status of a patient based on the determined density parameter, the elongated body being at least partially inserted within the patient.

Example 12J. The device of any of example 1J-11J, wherein the sensor comprises: a first ultrasonic sensor configured to transmit a first ultrasonic signal in a first direction through the fluid flowing distally within the lumen; and a second ultrasonic sensor configured to transmit a second ultrasonic signal in a second direction through the fluid flowing distally within the lumen, the second ultrasonic sensor being positioned on the elongated body proximal to the first ultrasonic sensor.

Example 13J. The system of any of examples 1J-12J, wherein the elongated body comprises a Foley catheter.

Example 1K. A method comprising: sensing, with a sensor located on an elongated body defining a lumen the elongated body comprising a proximal portion and a distal portion, at least one flow parameter of a fluid within the lumen; and determining, with processing circuitry, at least one of a density parameter or a temperature parameter of the fluid in the lumen based on the sensed at least one flow parameter of the fluid.

Example 2K. The method of example 1K, wherein the at least one flow parameter sensed by the sensor comprises an average transit time of the fluid through at least a portion of the lumen.

Example 3K. The method of any of examples 1K-2K, wherein the density parameter comprises at least one of a density of the fluid, a specific gravity of the fluid, a change in the density of the fluid, or a change in the specific gravity of the fluid.

Example 4K. The method of any of examples 1K-3K, wherein the temperature parameter comprises at least one of a temperature of the fluid or a change in the temperature of the fluid.

Example 5K. The method of any of examples 1K-4K, further comprising determining, with the processing circuitry, the at least one of the density parameter or the temperature parameter of the fluid in the lumen based on the sensed at least one flow parameter of the fluid and a geometry of the lumen.

Example 6K. The method of example 5K, wherein the geometry of the lumen includes a volume of at least a portion of the lumen.

Example 7K. The method of any of examples 1K-6K, further comprising determining, with a temperature sensor, a temperature of the fluid within the lumen, and determining, with the processing circuitry, the density parameter of the fluid based on the at least one flow parameter and the determined temperature of the fluid.

Example 8K. The method of example 7K, wherein the temperature sensor is located on the elongated body.

Example 9K. The method of example 1K, further comprising determining, with the processing circuitry, the density parameter of the fluid based on the at least one flow parameter and an estimated temperature of the fluid.

Example 10K. The method of example 9K, further comprising estimating the estimated temperature of the fluid based on a sensed body temperature of a patient in which the elongated body is at least partially inserted.

Example 11K. The method of any of examples 1K-10K, further comprising: determining the density parameter of the patient based on the sensed at least one flow parameter of the fluid, and determining a hydration status of a patient based on the determined density parameter, the elongated body being at least partially inserted within the patient.

Example 12K. The method of any of examples 1K-11K, further comprising: transmitting, with a first ultrasonic sensor, a first ultrasonic signal in a first direction through the fluid flowing distally within the lumen; and transmitting, with a second ultrasonic sensor, a second ultrasonic signal in a second direction through the fluid flowing distally within the lumen, the second ultrasonic sensor being positioned on the elongated body proximal to the first ultrasonic sensor.

Example 13K. The method of any of examples 1K-13K, wherein the elongated body comprises a Foley catheter.

Example 1L. A system comprising: an elongated body defining a lumen, the elongated body comprising a proximal portion and a distal portion; an anchoring member positioned on the proximal portion of the elongated body; a sensor located on the elongated body, the sensor configured to sense at least one flow parameter of a fluid within the lumen; processing circuitry configured to determine at least one of a density parameter or a temperature parameter of the fluid in the lumen based on the sensed at least one flow parameter of the fluid; and a temperature sensor configured to determine a temperature of the fluid within the lumen, wherein the processing circuitry is configured to determine the density parameter of the fluid based on the at least one flow parameter and the determined temperature of the fluid.

Example 1M. A catheter system, comprising: an elongated body defining a lumen, the elongated body comprising a proximal portion and a distal portion; an anchoring member positioned on the proximal portion of the elongated body; at least one sensor configured to be coupled to the elongated body, the at least one sensor configured to sense one or more parameters of a fluid within the lumen of the elongate body; and memory configured to be coupled to the elongated body, the memory configured to store sensor calibration information, wherein the system is configured to calibrate the at least one sensor based on the sensor calibration information stored by the memory.

Example 2M. The system of example 1M, wherein the sensor calibration information is specific calibration information for the elongated body and/or the at least one sensor.

Example 3M. The system of any of examples 1M-2M, wherein the at least one sensor is a flow sensor configured to sense a flow rate of the fluid in the lumen.

Example 4M. The system of example 3M, wherein the flow sensor comprises: a first temperature sensor configured to sense a first temperature of the fluid at a first location in the lumen; a second temperature sensor configured to sense a second temperature of the fluid at a second location in the lumen, the first location being proximal to the second location; and a heating member located proximal to the second temperature sensor, the heating member configured to heat the fluid within the lumen; wherein the flow sensor determines the flow rate based on the first temperature, the second temperature and the sensor calibration information.

Example 5M. The system of example 4M, wherein the sensor calibration information includes at least one of manufacturing variances in the dimensions of the lumen, a position of the heating member on the elongated body, a position of the first temperature sensor on the elongated body, a position of the second temperature sensor on the elongated body, manufacturing variances of the heating member, manufacturing variances of the first temperature sensor, manufacturing variances of the second temperature sensor or a constitution of the substance of interest within the lumen.

Example 6M. The system of example 1M, wherein the at least one sensor is a flow sensor configured to sense a flow rate of the fluid with the lumen.

Example 7M. The system of example 6M, wherein the flow sensor comprises:
a first ultrasonic sensor configured to transmit a first ultrasonic signal in a first direction through the fluid flowing distally within the lumen; and a second ultrasonic sensor configured to transmit a second ultrasonic signal in a second direction through the substance of interest flowing distally within the lumen, the second ultrasonic sensor being positioned on the elongated body proximal to the first ultrasonic sensor; wherein the first ultrasonic sensor is configured to receive the second ultrasonic signal transmitted through the fluid flowing in the lumen; wherein the second ultrasonic sensor is configured to receive the first ultrasonic sound transmitted through the fluid flowing in the lumen; wherein the flow sensor determines the flow rate based on a first transit time of the first ultrasonic signal, a second transit time of the second ultrasonic signal and the sensor calibration information; wherein the memory is located on the sensor that is removably coupled to the elongated body.

Example 8M. The system of example 7M, wherein the sensor calibration information may be at least one of: dimensions of the lumen, a position of the first ultrasonic sensor on the elongated body, a position of the second ultrasonic sensor on the elongated body, manufacturing variances of the first ultrasonic sensor, manufacturing variances of the second ultrasonic sensor or a constitution of the fluid in the lumen.

Example 9M. The system of example 1M, wherein the at least one sensor includes an oxygen sensor configured to sense the amount of oxygen within the fluid in the lumen.

Example 10M. The system of example 9M, wherein the oxygen sensor comprises: a fluorescence material configured to be located within the lumen with the fluid in the lumen; a light source configured to emit light to expose the fluorescence material to the emitted light, wherein the fluorescence material within the fluid is configured to fluoresce when exposed to the light in the lumen; and a light detector configured to detect the fluorescence of the fluorescence material, wherein the device is configured to detect oxygen in the fluid within the lumen based on the detected fluorescence.

Example 11M. The system of example 11M, wherein the sensor calibration information may be at least one of: dimensions of the lumen, fluorescing properties of the fluoresce material, manufacturing variances of the fluoresce material, manufacturing variances of the light source or manufacturing variances of the light receptor.

Example 12M. The system of any of examples 1M-11M, wherein the elongated body comprises a Foley catheter.

Example 13M. The system of any of examples 1M-12M, wherein the memory is stored on the at least one sensor.

Example 14M. The system of any of examples 1M-12M, wherein the memory is separate from the at least one sensor.

Example 1N. A method comprising: sensing, with at least one sensor configured to be coupled to an elongated body defining a lumen the elongated body comprising a proximal portion and a distal portion, one or more parameters of a fluid within the lumen of the elongate body; storing, with a memory configured to be coupled to the elongated body, sensor calibration information; and calibrating the at least one sensor based on sensor calibration information stored by the memory.

Example 2N. The method of example 1N, wherein the sensor calibration information is calibration information specific to the at least one sensor.

Example 3N. The method of any of examples 1N-2N, further comprising sensing a flow rate of the substance of interest in the lumen where the at least one sensor is a flow sensor.

Example 4N. The method of example 3N, further comprising: sensing, with a first temperature sensor, a first temperature of the substance of interest at a first location in the lumen; sensing, with a second temperature sensor, a second temperature of the substance of interest at a second location in the lumen, the first location being proximal to the second location; and heating, with a heating member located proximal to the second temperature sensor, the substance of interest within the lumen; determining, with the flow sensor, the flow rate based on the first temperature, the second temperature and the sensor calibration information.

Example 5N. The method of example 1N, further comprising sensing, with a flow sensor, a flow rate of a liquid with the lumen.

Example 6N. The method of example 5M, further comprising: transmitting, with a first ultrasonic sensor, a first ultrasonic signal in a first direction through the substance of interest flowing distally within the lumen; and transmitting, with a second ultrasonic sensor, a second ultrasonic signal in a second direction through the substance of interest flowing distally within the lumen, the second ultrasonic sensor being positioned on the elongated body proximal to the first ultrasonic sensor; receiving, with the first ultrasonic sensor, the second ultrasonic signal transmitted through the substance of interest flowing in the lumen; receiving, with the second ultrasonic sensor, the first ultrasonic sound transmitted through the substance of interest flowing in the lumen; determining, with the flow sensor, the flow rate based on a first transit time of the first ultrasonic signal, a second transit time of the second ultrasonic signal and the sensor calibration information.

Example 7N. The method of example 1N, further comprising sensing, with an oxygen sensor, the amount of oxygen within a substance of interest in the lumen.

Example 8N. The method of example 7N, further comprising: emitting, with a light source, light to expose a fluorescence material configured to be located within the lumen with the substance of interest in the lumen, wherein the fluorescence material within the substance of interest is configured to fluoresce when exposed to the light in the lumen; and detecting, with a light detector, the fluorescence of the fluorescence material; and detecting, with the oxygen sensor, oxygen in the substance of interest within the lumen based on the detected fluorescence.

Example 1O. A catheter system, comprising: an elongated body defining a lumen, the elongated body comprising a proximal portion and a distal portion; an anchoring member positioned on the proximal portion of the elongated body; a flow sensor configured to sense a flow rate of the fluid in the lumen; an oxygen sensor configured to sense the amount of oxygen within the fluid in the lumen; and memory configured to be coupled to the elongated body, the memory configured to store sensor calibration information, wherein the system is configured to calibrate the flow sensor and/or the oxygen sensor based on the sensor calibration information stored by the memory.

Example 2O. The system of example 1O, wherein the memory is configured to be coupled to one of the flow sensor or the oxygen sensor.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements.

What is claimed is:

1. A system comprising:
    an elongated body defining a lumen, the elongated body comprising a proximal portion and a distal portion, the proximal portion being configured to be at least partially inserted into a body of a patient and the distal portion being configured to remain external to the body of the patient when the proximal portion is at least partially inserted into the body of the patient;
    an anchoring member positioned on the proximal portion of the elongated body;
    a sensor located on the distal portion of the elongated body, the sensor configured to sense at least one flow parameter of a fluid within the lumen;
    a temperature sensor located on the elongated body, the temperature sensor being configured to sense a body temperature of a patient or a temperature of the fluid within the lumen; and
    processing circuitry configured to determine a density parameter of the fluid in the lumen based at least in part on the sensed at least one flow parameter of the fluid and one of the sensed body temperature of the patient or the sensed temperature of the fluid.

2. The system of claim 1, wherein the at least one flow parameter sensed by the sensor comprises an average transit time of the fluid through at least a portion of the lumen.

3. The system of claim 1, wherein the density parameter comprises at least one of a density of the fluid, a specific gravity of the fluid, a change in the density of the fluid, or a change in the specific gravity of the fluid.

4. The system of claim 1, wherein the processing circuitry is configured to determine the density parameter of the fluid in the lumen based on the sensed at least one flow parameter of the fluid and a geometry of the lumen.

5. The system of claim 4, wherein the geometry of the lumen includes a volume of at least a portion of the lumen.

6. The system of claim 1, wherein the temperature sensor is configured to sense the temperature of the fluid within the lumen, wherein the processing circuitry is configured to determine the density parameter of the fluid based on the at least one flow parameter and the sensed temperature of the fluid.

7. The system of claim 1, wherein the temperature sensor is configured to sense the body temperature of the patient, wherein the processing circuitry is further configured to determine an estimated temperature of the fluid based on the sensed body temperature of the patient, and wherein the density parameter of the fluid is based on the at least one flow parameter and the estimated temperature of the fluid.

8. The system of claim 1, wherein the fluid comprises urine.

9. A method comprising:
sensing, with a sensor located on a distal portion an elongated body defining a lumen, the elongated body comprising a proximal portion and the distal portion, the proximal portion being configured to be at least partially inserted into a body of a patient and the distal portion being configured to remain external to the body of the patient when the proximal portion is at least partially inserted into the body of the patient, at least one flow parameter of a fluid within the lumen;
sensing, with a temperature sensor located on the elongated body, a body temperature of a patient or a temperature of the fluid within the lumen; and
determining, with processing circuitry, a density parameter of the fluid in the lumen based at least in part on the sensed at least one flow parameter of the fluid and one of the sensed body temperature of the patient or the sensed temperature of the fluid.

10. The method of claim 9, wherein the at least one flow parameter sensed by the sensor comprises an average transit time of the fluid through at least a portion of the lumen.

11. The method of claim 9, wherein the density parameter comprises at least one of a density of the fluid, a specific gravity of the fluid, a change in the density of the fluid, or a change in the specific gravity of the fluid.

12. The method of claim 9, wherein determining, with the processing circuitry, the density parameter of the fluid in the lumen comprises determining the density parameter based on the sensed at least one flow parameter of the fluid and a geometry of the lumen.

13. The method of claim 12, wherein the geometry of the lumen includes a volume of at least a portion of the lumen.

14. The method of claim 9, wherein sensing the body temperature or the temperature of the fluid comprises sensing the temperature of the fluid within the lumen, and wherein determining the density parameter of the fluid comprises determining the density parameter of the fluid based on the at least one flow parameter and the sensed temperature of the fluid.

15. The method of claim 9, wherein sensing the body temperature or the temperature of the fluid comprises sensing the body temperature of the patient, the method further comprising determining, with the processing circuitry, an estimated temperature of the fluid based on the sensed body temperature of the patient, wherein determining the density parameter of the fluid comprises determining the density parameter based on the at least one flow parameter and the estimated temperature of the fluid.

16. The method of claim 9, wherein the elongated body is part of a Foley catheter.

17. The method of claim 9, wherein the fluid comprises urine.

18. A Foley catheter system comprising:
a Foley catheter elongated body defining a drainage lumen, the Foley catheter elongated body comprising a proximal portion and a distal portion, the proximal portion being configured to be at least partially inserted into a body of a patient and the distal portion being configured to remain external to the body of the patient when the proximal portion is at least partially inserted into the body of the patient;
an anchoring member positioned on the proximal portion of the Foley catheter elongated body;
a sensor located on the distal portion of the Foley catheter elongated body, the sensor configured to sense at least one flow parameter of a fluid within the lumen;
processing circuitry configured to determine at least one of a density parameter or a temperature parameter of the fluid in the lumen based on the sensed at least one flow parameter of the fluid; and
a temperature sensor located on the Foley catheter elongated body and being configured to sense a temperature of the fluid within the lumen, wherein the processing circuitry is configured to determine the density parameter of the fluid based on the at least one flow parameter and the sensed temperature of the fluid.

19. The system of claim 18, further comprising a Foley catheter including the Foley catheter elongated body and the anchoring member.

20. The system of claim 18, wherein the fluid comprises urine.

* * * * *